United States Patent [19]

Petrillo, Jr. et al.

[11] Patent Number: 4,462,943

[45] Date of Patent: Jul. 31, 1984

[54] CARBOXYALKYL AMINO ACID DERIVATIVES OF VARIOUS SUBSTITUTED PROLINES

[75] Inventors: Edward W. Petrillo, Jr.; Eric M. Gordon, both of Pennington; John Krapcho, Somerset; Peter W. Sprague, Pennington, all of N.J.

[73] Assignee: E. R. Squibb & Sons, Inc., Princeton, N.J.

[21] Appl. No.: 306,553

[22] Filed: Sep. 28, 1981

Related U.S. Application Data

[63] Continuation-in-part of Ser. No. 209,563, Nov. 24, 1980, abandoned.

[51] Int. Cl.³ .................. C07C 103/52; A61K 37/00; A61K 31/40
[52] U.S. Cl. .................. 260/112.5 R; 424/177; 424/274; 548/533
[58] Field of Search ................ 260/112.5 R; 424/177, 424/274; 548/533

[56] References Cited

U.S. PATENT DOCUMENTS

| 4,105,776 | 8/1978 | Ondetti et al. | 424/274 |
| 4,154,935 | 5/1979 | Ondetti et al. | 546/189 |
| 4,217,359 | 8/1980 | Krapcho | 424/274 |

FOREIGN PATENT DOCUMENTS

| 12401 | 6/1980 | European Pat. Off. |
| 2027025 | 2/1980 | United Kingdom. |
| 2028327 | 3/1980 | United Kingdom. |
| 2039478 | 8/1980 | United Kingdom. |

Primary Examiner—Delbert R. Phillips
Attorney, Agent, or Firm—Lawrence S. Levinson; Stephen B. Davis

[57] ABSTRACT

Carboxyalkyl dipeptides of the formula

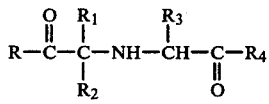

wherein $R_4$ is a 3-, 4-, 5-, or 4,4-substituted proline are disclosed. These compounds are useful as hypotensive agents due to their angiotensin converting enzyme inhibition activity.

6 Claims, No Drawings

CARBOXYALKYL AMINO ACID DERIVATIVES OF VARIOUS SUBSTITUTED PROLINES

RELATED APPLICATIONS

This application is a continuation-in-part of U.S. Ser. No. 209,563 filed Nov. 24, 1980, now abandoned.

BACKGROUND OF THE INVENTION

Patchett et al. in European Patent Application No. 12,401 disclose that carboxyalkyl depeptide derivatives of the formula

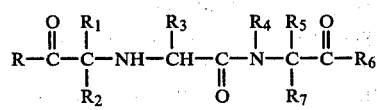

are useful antihypertensive agents due to their ability to inhibit the angiotensin converting enzyme. Among the compounds disclosed by Patchett et al. are those wherein $R_4$ and $R_5$ join together to form an alkylene bridge of from 2 to 3 carbons and one sulfur atom, an alkylene bridge of from 3 to 4 carbons containing a double bond or an alkylene bridge as above substituted with a hydroxy, lower alkoxy, lower alkyl, or di(lower alkyl) group.

Mercaptoacyl derivatives of proline and substituted prolines are known to be useful hypotensive agents due to their angiotensin converting enzyme inhibition activity. Ondetti et al. in U.S. Pat. No. 4,105,776 disclose such compounds wherein the proline ring is unsubstituted or substituted by an alkyl or hydroxy group. Ondetti et al. in U.S. Pat. No. 4,154,935 disclose such compounds wherein the proline ring is substituted with one or more halogens. Ondetti et al. in U.K. Patent Application No. 2,028,327 disclose such compounds wherein the proline ring is substituted by various ethers and thioethers. Krapcho is U.S. Pat. No. 4,217,359 disclose such compounds wherein the proline ring has a carbamoyloxy substituent. Krapcho in U.K. Patent Application No. 2,039,478 and U.S. Ser. No. 99,164 filed Nov. 30, 1979, now U.S. Pat. No. 4,311,697, discloses such compounds wherein the proline ring has a diether, dithioether, ketal or thioketal substituent in the 4-position. Krapcho in U.S. Ser. No. 164,985 filed July 1, 1980, now U.S. Pat. No. 4,316,905, discloses such compounds wherein the proline ring has a cycloalkyl, phenyl, or phenyl-lower alkylene substituent. Ondetti et al. in U.S. Ser. No. 51,772 filed June 25, 1979, now U.S. Pat. No. 4,234,489, disclose such compounds wherein the proline has a keto substituent in the 5-position. Krapcho et al. in U.S. Ser. No. 162,341 filed June 23, 1980, now U.S. Pat. No. 4,310,461 disclose such compounds wherein the proline has an imido, amido, or amino substituent in the 4-position. Iwao et al. in U.K. Patent Application No. 2,027,025 disclose such compounds wherein the proline has a phenyl or a 2- or 4-hydroxyphenyl substituent in the 5-position.

SUMMARY OF THE INVENTION

This invention is directed to new substituted or unsubstituted carboxyalkyl amino acid derivatives of substituted prolines of formula I and salts thereof

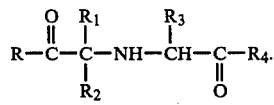

$R_4$ is a substituted proline of the formula

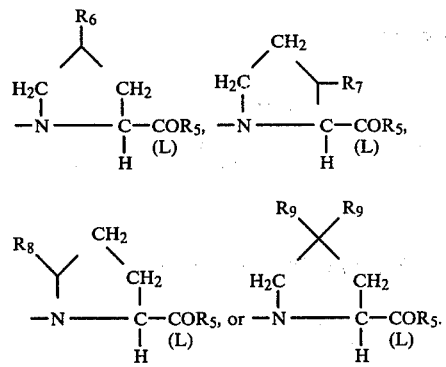

$R_6$ is halogen, keto, azido,

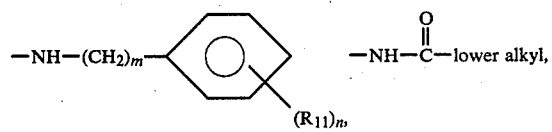

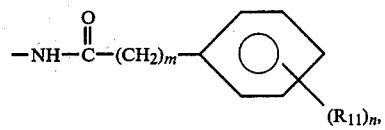

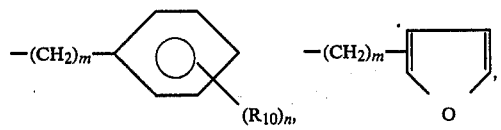

a 1- or 2-naphthyl of the formula

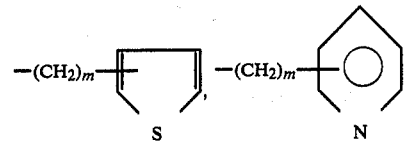

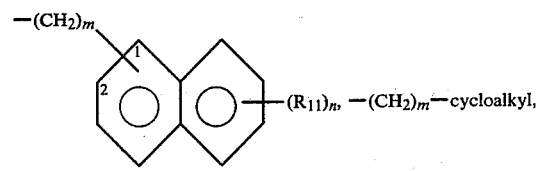

a 1- or 2- naphthyloxy of the formula

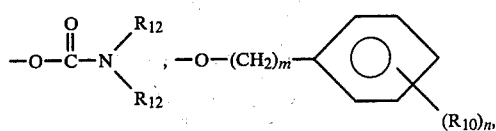

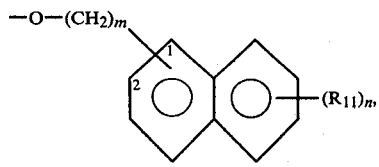

—S-lower alkyl,

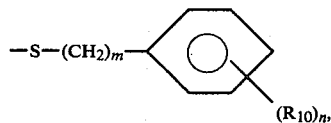

or a 1- or 2-naphthylthio of the formula

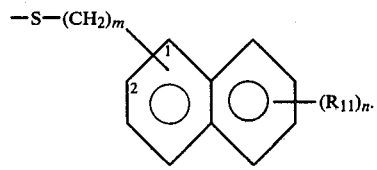

R₇ is keto, halogen,

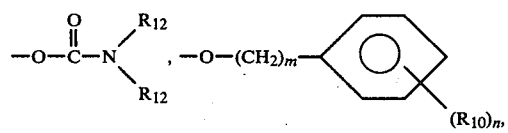

a 1- or 2-naphthloxy of the formula

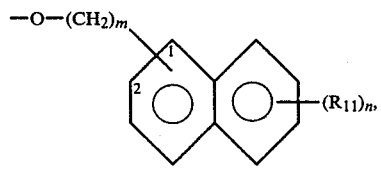

—S-lower alkyl,

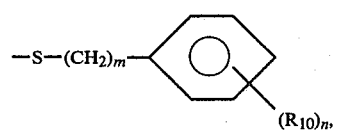

or a 1- or 2-naphthylthio of the formula

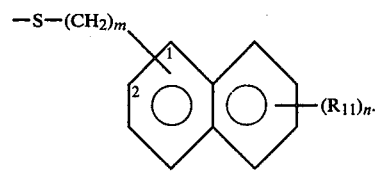

R₈ is keto or

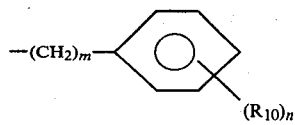

R₉ is halogen or —Y—R₁₃.

m is zero, one, two, or three.

R₁₀ is hydrogen, lower alkyl of 1 to 4 carbons, lower alkoxy of 1 to 4 carbons, lower alkylthio of 1 to 4 carbons, chloro, bromo, fluor, trifluoromethyl, hydroxy, phenyl, phenoxy, phenylthio, or phenylmethyl.

R₁₁ is hydrogen, lower alkyl of 1 to 4 carbons, lower alkoxy of 1 to 4 carbons, lower alkylthio of 1 to 4 carbons, bromo, fluoro, trifluoromethyl, or hydroxy.

n is one, two or three provided that n is more than one only if R₁₀ or R₁₁ is hydrogen, methyl, methoxy, chloro, or fluoro.

R₁₂ is hydrogen or lower alkyl of 1 to 4 carbons.

Y is oxygen or sulfur.

R₁₃ is lower alkyl of 1 to 4 carbons,

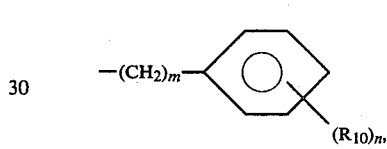

or the R₁₃ group join to complete an unsubstituted 5- or 6-membered ring or said ring in which one or more of the carbons has a lower alkyl of 1 to 4 carbons, or a di (lower alkyl of 1 to 4 carbons) substituent.

R and R₅ are independently selected from hydroxy, lower alkoxy, di(lower alkyl)-amino-lower alkoxy, such as dimethylaminoethoxy, lower alkyl-carbonyl-amino-lower alkoxy, such as acetylaminoethoxy, lower alkyl-carbonyloxy-lower alkoxy, such as pivaloyloxymethoxy,

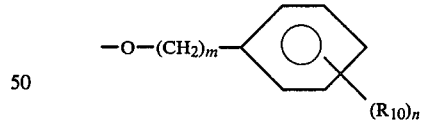

wherein m, n and R₁₀ are as defined above, amino, lower alkyl-amino, di(lower alkyl)-amino, hydroxyamino, benzylamino, or phenethylamino.

R₁ is hydrogen, lower alkyl,

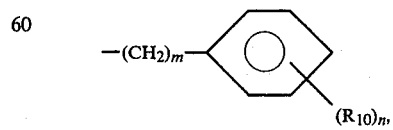

halo substituted lower alkyl, hydroxy substituted lower alky, —(CH₂)$_g$—cycloalkyl, —(CH₂)$_q$-carboxy, —(CH₂)$_q$—S-lower alkyl,

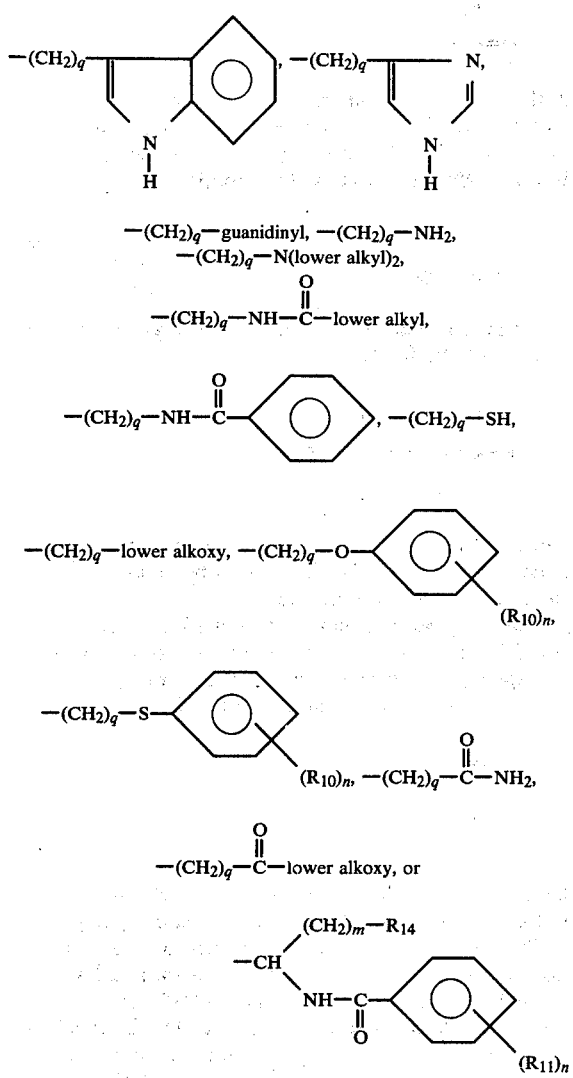

—(CH$_2$)$_q$—guanidinyl, —(CH$_2$)$_q$—NH$_2$,
—(CH$_2$)$_q$—N(lower alkyl)$_2$, —(CH$_2$)$_q$—NH—C(=O)—lower alkyl,

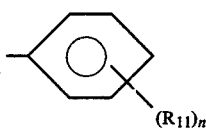, —(CH$_2$)$_q$—SH,

—(CH$_2$)$_q$—lower alkoxy, —(CH$_2$)$_q$—O—[phenyl](R$_{10}$)$_n$,

—(CH$_2$)$_q$—S—[phenyl](R$_{10}$)$_n$, —(CH$_2$)$_q$—C(=O)—NH$_2$,

—(CH$_2$)$_q$—C(=O)—lower alkoxy, or

—CH(—(CH$_2$)$_m$—R$_{14}$)(NH—C(=O)—[phenyl](R$_{11}$)$_n$)

wherein m, n, R$_{10}$ and R$_{11}$ are as defined above, R$_{14}$ is lower alkyl, cycloalkyl, or [phenyl](R$_{11}$)$_n$
and q is an integer from 1 to 4.

R$_2$ is hydrogen or lower alkyl.

R$_3$ is hydrogen, lower alkyl, halo substituted lower alkyl, hydroxy substituted lower alkyl, —(CH$_2$)$_q$—NH$_2$, —(CH$_2$)$_q$13 N-(lower alkyl)$_2$, —(CH$_2$)$_q$—guanidinyl, —(CH$_2$)$_q$—SH, —(CH$_2$)$_q$—S-lower alkyl,

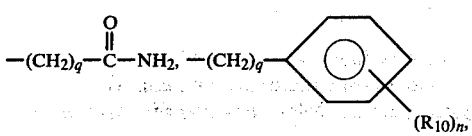

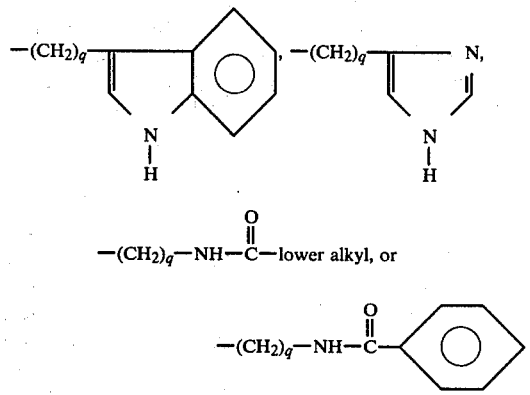

—(CH$_2$)$_q$—NH—C(=O)—lower alkyl, or

—(CH$_2$)$_q$—NH—C(=O)—[phenyl]

wherein R$_{10}$, n and q are as defined above.

DETAILED DESCRIPTION OF THE INVENTION

This invention in its broadest aspects relates to the carboxyalkyl dipeptide substituted prolines of formula I above, to compositions containing such compounds and to the method of using such compounds as anti-hypertensive agents.

The term lower alkyl used in defining various symbols refers to straight or branched chain hydrocarbon radicals having up to seven carbons, for example, methyl, ethyl, propyl, isopropyl, butyl, isobutyl, t-butyl, pentyl, isopentyl, etc. The preferred lower alkyl groups are up to four carbons with methyl and ethyl most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term hydroxy substituted lower alkyl refers to such lower alkyl groups described above in which one or more hydrogens have been replaced by a hydroxy group such as hydroxymethyl, 1-hydroxyethyl, 2-hydroxyethyl, etc.

The compounds of formula I can be prepared according to the general procedures outlined by Patchett et al. in European Patent Application No. 12,401. For example, the compounds wherein R$_2$ is hydrogen can preferably be prepared by reacting the keto compound of the formula

 (II)

with the dipeptide of the formula

 (III)

in an aqueous solution or in an organic solvent such as acetonitrile and in the presence of sodium cyano borohydride.

When the proline ring is not substituted by a divalent sulfur, instead of performing the reaction in one-step, the intermediate Schiff base, enamine, or aminol resulting from the reaction of II and III can be isolated and catalytically reduced to yield the desired product. Suitable catalytic reducing agents are hydrogen in the presence of 10% palladium on carbon, freshly prepared palladium black, or Raney nickel.

In these procedures and those described below, when R and $R_5$ are carboxy protecting groups such as alkoxy or benzyloxy or the like, they can be converted by known methods such as hydrolysis or hydrogenation to the products wherein R and/or $R_5$ are hydroxy. Reductive cleavage of the diester product wherein $R_5$ is benzyloxy and R is alkoxy yields the monoester product wherein $R_5$ is hydroxy and R is alkoxy. Similarly, reductive cleavage of the diester product wherein $R_5$ is alkoxy and R is benzyloxy yields the monoester product wherein $R_5$ is alkoxy and R is hydroxy.

The compounds of formula I wherein $R_2$ is hydrogen can also be prepared by reacting the keto compound of formula II with the amino acid of the formula

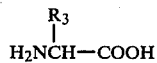  (IV)

in the presence of sodium cyano borohydride to yield the intermediate of the formula

  (V)

In this reaction, an ester, such as the t-butyl ester, of the amino acid of formula IV can be employed. The ester function is then removed following completion of the reaction to give the intermediate of formula V. The intermediate of formula V is then coupled with the substituted proline of the formula

H—$R_4$  (VI)

to yield the desired dipeptide products. This reaction can be performed in the presence of a coupling agent such as dicyclohexylcarbodiimide or diphenylphosphoryl azide. Alternatively, the intermediate of formula V can be converted to an activated ester form such as that derived from 1-hydroxybenzotriazole. If either or both of the $R_1$ and $R_3$ substituents has a free amino group, this group is protected by conversion to the corresponding N-formyl, N-butoxycarbonyl, or N-carbobenzyloxy prior to the coupling reaction.

The compounds of formula I wherein $R_2$ is hydrogen or lower alkyl can be prepared by reacting the amino acid (or ester, amide, or hydroxamic acid) of the formula

  (VII)

with the ketone of the formula

  (VIII)

in the presence of sodium cyano borohydride.

Alternatively, this reaction can be performed in a step-wise fashion by reacting the amino acid of formula VII with the keto acid of the formula

  (IX)

in the presence of the reducing agent to yield the intermediate of the formula

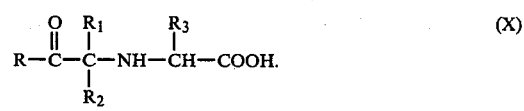  (X)

The intermediate of formula X is then coupled with the amino acid of formula VI as described above to yield the desired dipeptide product.

The dipeptide products of formula I can also be prepared by alkylating the dipeptide of formula III with the appropriate α-haloacid (ester or amide) or α-sulfonyloxy acid (ester or amide) of the formula

  (XI)

under basic conditions wherein X is chloro, bromo, iodo, an alkyl sulfonyloxy or an aryl sulfonyloxy.

This reaction can also be performed in a stepwise fashion by treating the amino acid of formula IV with the α-haloacid or α-sulfonyloxy acid of formula XI to yield the intermediate of formula X. The intermediate of formula X is then coupled with the amino acid of formula VI as described above to yield the desired dipeptide product.

The products of formula I can also be prepared by alkylating the amino acid (or ester, amide, or hydroxamic acid) of formula VII with the appropriate α-haloacetyl or α-sulfonyloxy acetyl amino acid of the formula

  (XII)

under basic conditions wherein X is as defined above.

Again, this preparation can be performed in a stepwise fashion by reacting the amino acid (or ester, amide, or hydroxamic acid) of formula VII with a α-haloacetic acid or α-sulfonyloxy acetic acid of the formula

  (XIII)

to yield the intermediate of formula X.

The dipeptide intermediate of formula III can be obtained by reacting the N-protected amino acid of the formula

(XIV)

wherein the N-protecting group is benzyloxycarbonyl, t-butoxycarbonyl, or p-methoxybenzyloxycarbonyl with the substituted proline of formula VI. Removal of the N-protecting group yields the intermediate of formula III.

Similarly, the ketone intermediate of formula VIII can be obtained by reacting the keto acid of formula IX with the substituted proline of formula VI.

The various substituted prolines of formula VI are described in the literature or in the pending U.S. patent applications referred to above. When the proline is known in the acid form it can be readily converted to the ester by conventional means. For example, the esters where $R_5$ is t-butyloxy can be obtained by treating the corresponding N-carbobenzyloxyproline with isobutylene under acidic conditions and then removing the N-carbobenzyloxy protecting group by catalytic hydrogenation and the esters wherein $R_5$ is benzyloxy can be obtained by treating the proline compound with benzyl alcohol and thionly chloride.

Various substituted prolines are disclosed by Mauger et al., Chem. Review, Vol. 66, p. 47–86 (1966). Ondetti et al. disclose various halogen, ether and thioether substituted prolines in U.S. Pat. No. 4,154,935 and U.K. Application No. 2,028,327. Iwao et al. in U.K. Application No. 2,027,025 disclose various 5-substituted prolines. Krapcho in U.S. Pat. No. 4,217,359 discloses various carbamoyloxy substituted prolines. Krapcho in U.S. Ser. No. 99,164, now U.S. Pat. No. 4,311,697, and U.K. Pat. Application No. 2,039,478 discloses various diether, dithioether, ketal, and thioketal substituted prolines.

As disclosed by Krapcho in U.S. Ser. No. 164,985, now U.S. Pat. No. 4,316,905, the subtituted prolines wherein $R_6$ is

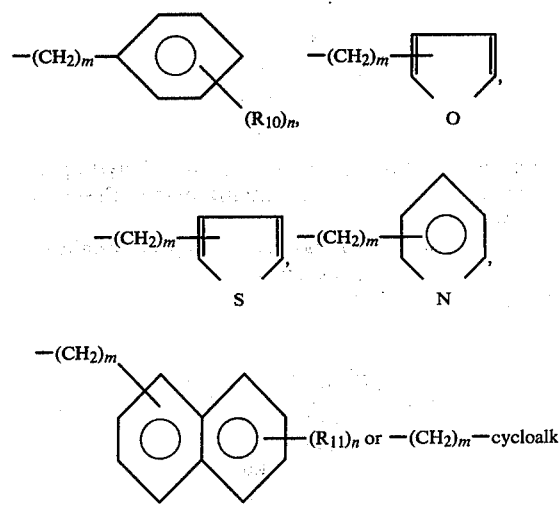

are prepared by reacting a 4-keto proline of the formula

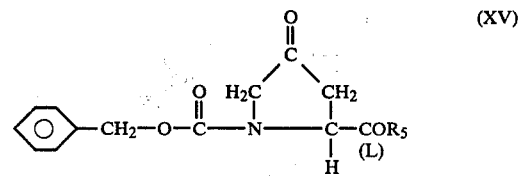

(XV)

with a solution of the Grignard or lithium reagent $R_6$—Mg—halo or $R_6$—Li    (XVI)

wherein $R_6$ is as defined above and halo is Br or Cl to yield

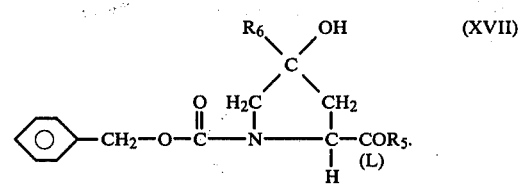

(XVII)

This compound is treated with a dehydrating agent such as p-toluenesulfonic acid, sulfuric acid, potassium bisulfate, or trifluoroacetic acid to yield the 3,4-dehydro-4-substituted proline of the formula

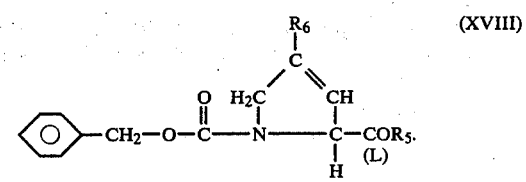

(XVIII)

Removal of the N-benzyloxycarbonyl protecting group and hydrogenation of the compound of formula XVIII yields the desired starting materials. The substituted proline wherein $R_6$ is cyclohexyl can be prepared by further hydrogenation of the 4-phenyl proline compound.

As disclosed by Krapcho et al. in U.S. Ser. No. 162,341, now U.S. Pat. No. 4,310,461, the substituted proline wherein $R_6$ is

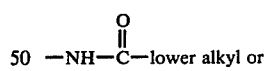

—NH—C(=O)—lower alkyl or

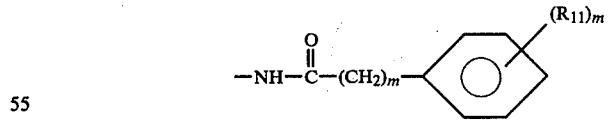

can be prepared by acylating the corresponding amino substituted proline.

The compounds of formula I wherein $R_6$ is

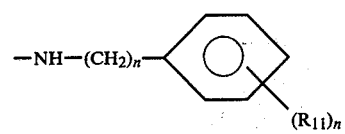

are prepared by employing a proline of the formula

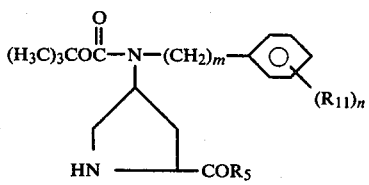

(XIX)

in the above reaction schemes. Removal of the t-butoxycarbonyl protecting group by treatment with trifluoroacetic acid at the end of the reaction sequence yields the desired compounds of formula I.

The substituted proline of formula XIX can be obtained by treating the 4-keto proline of formula XV under reductive conditions with the amine of the formula

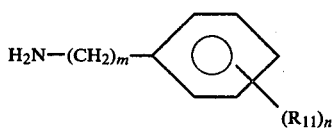

(XX)

followed by introduction of t-butoxycarbonyl group. Removal of the N-benzyloxycarbonyl protecting group from the proline nitrogen yields the substituted proline of formula XIX.

Preferred compounds of this invention with respect to the proline portion of the structure of formula I are those wherein:

$R_5$ is hydroxy.
$R_6$ is chloro or fluoro.
$R_6$ is cyclohexyl.
$R_6$ is

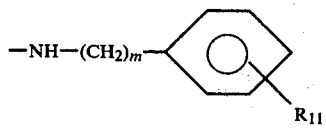

wherein m is zero, one, or two and $R_{11}$ is hydrogen, methyl, methoxy, methylthio, chloro, bromo, fluoro, trifluromethyl, or hydroxy.

$R_6$ is

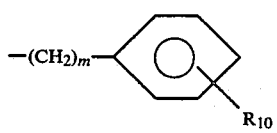

wherein m is zero, one or two and $R_{10}$ is hydrogen, methyl, methoxy, methylthio, chloro, bromo, fluoro, or hydroxy.

$R_6$ is

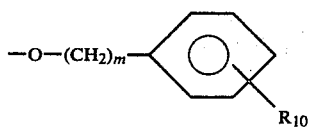

wherein m is zero, one, or two and $R_{10}$ is hydrogen, methyl, methoxy, methylthio, chloro, bromo, fluoro, or hydroxy.

$R_6$ is a 1- or 2-naphthyloxy of the formula

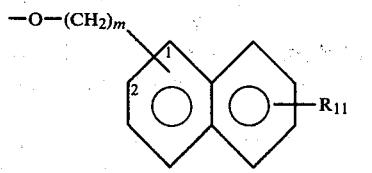

wherein m is zero, one or two and $R_{11}$ is hydrogen, methyl, methoxy, methylthio, chloro, bromo, fluoro, trifluoromethyl, or hydroxy.

$R_6$ is —S-lower alkyl wherein lower alkyl is straight or branched chain of 1 to 4 carbons.

$R_6$ is

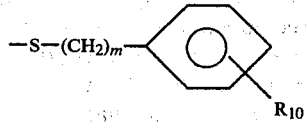

wherein m is zero, one, or two and $R_{10}$ is hydrogen, methyl, methoxy, methylthio, chloro, bromo, fluoro, or hydroxy.

$R_6$ is a 1- or 2-naphthylthio of the formula

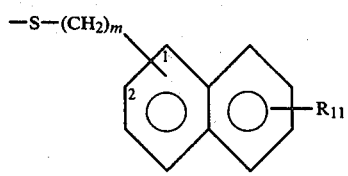

wherein m is zero, one or two and $R_{11}$ is hydrogen, methyl, methoxy, methylthio, chloro, bromo, fluoro, trifluoromethyl, or hydroxy.

$R_7$ is

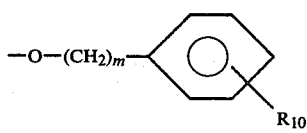

wherein m is zero, one or two and $R_{10}$ is hydrogen, methyl, methoxy, methylthio, chloro, bromo, fluoro or hydroxy.

$R_7$ is —S-lower alkyl and lower alkyl is straight or branched chain of 1 to 4 carbons.

$R_7$ is

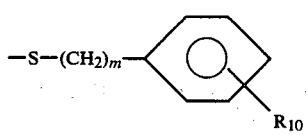

wherein m is zero, one, or two and $R_{10}$ is hydrogen, methyl, methoxy, methylthio, chloro, bromo, fluoro, or hydroxy.

R8 is phenyl, 2-hydroxyphenyl, or 4-hydroxyphenyl.

R9 are both chloro or fluoro.

R9 are both —Y—R13 wherein Y is O or S, R13 is straight or branched chain lower alkyl of 1 to 4 carbons or the R13 groups join to complete an unsubstituted 5- or 6-membered ring or said ring in which one or more of the carbons has a methyl or dimethyl substituent.

Preferred compounds of this invention with respect to the carboxyalkylpeptide portion of the structure of formula I are those wherein:

R is hydroxy, lower alkoxy of 1 to 4 carbons, or benzyloxy, especially ethoxy.

R1 is lower alkyl of 1 to 4 carbons

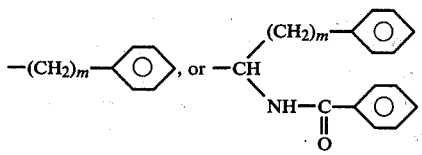

and m is one, two or three; especially phenylethyl.

R2 is hydrogen.

R3 is methyl, —(CH2)4—NH2, hydroxymethyl, benzyl, mercaptomethyl,

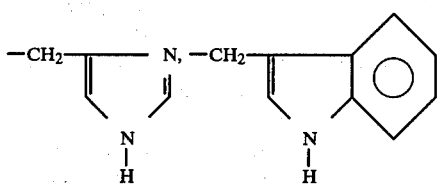

fluoromethyl, methylthioethyl, (4-hydroxyphenyl)methyl, or

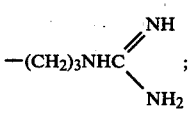

especially methyl.

As shown above, the proline portion of the molecule of the products of formula I is in the L-configuration. Depending upon the definition of $R_1$, $R_2$, and $R_3$ a second or third asymmetric center may also be present. The compounds accordingly can exist in diastereoisomeric forms or in mixtures thereof. The above described processes can utilize racemates, enantiomers of diastereomers as starting materials. When diastereomeric products are prepared, they can be separated by conventional chromatographic or fractional crystallization methods. In general, the aminoacid part-structures

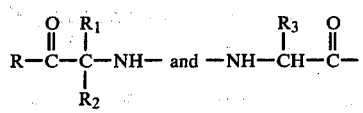

are preferred in the S-configuration.

The products of formula I wherein the proline ring is monosubstituted give rise to cis-trans isomerism. The configuration of the final product will depend upon the configuration of the $R_6$, $R_7$ and $R_8$ substituent in the starting material of formula VI.

The compounds of this invention form basic salts with a variety of inorganic or organic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose, for example, ammonium salts, aralkylamines like, dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantylmine, benzathine, or salts derived from amino acids like arginine, lysine or the like. The physiologically acceptable salts like the sodium or potassium salts and the amino acid salts can be used medicinally as described below and are preferred. These and other salts which are not necessarily physiologically acceptable are useful in isolating or purifying a product acceptable for the purposes described below. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of formula I including their pharmaceutically acceptable salts are useful as hypotensive agents. They inhibit the conversion of the decapeptide angiotensin I to angiotensin II and, therefore, are useful in relieving angiotensin related hypertension. The action of the enzyme renin on angiotensin, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen → (renin) → angiotensin I → (ACE) → angiotensin II sequence by inhibiting angiotensin converting enzyme and reducing or eliminating the formation of the pressor substance angiotensin II. Thus by the administration of a composition containing one, or a combination of compounds of formula I angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is apropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in a effective amount which comprises (for a 70 kg. mammal) a total daily dosage of about 30 to 600 mg., perferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroglumethiazide, bendroflumethiazide, methchlothiazide, trichlorothiazide, polythiazide or benthiazide, as well as ethacrynic acid, ticrynafen, chlorthalidone, furosemide, musolimine, bumetanide, riamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc. in a unit dosage form as called for by accepted pharmaceutical practice. The amount of active substance in these compositions or preparations is such that a suitable dosage in the range indicated is obtained.

Illustrated practice details are set forth in the following examples for the various reactions. These examples are preferred embodiments and also serve a models for the preparation of other compounds of this invention. The temperatures are given in degrees on the centigrade scale.

EXAMPLE 1

1-[N-(-b 1(S)-Ethoxycarbonyl-3-phenylpropyl)-L-alanyl]-4-[ethylenebis(thio)]-L-proline (a) 4-[Ethylenebis(thio)]-L-proline, tert. butyl ester A mixture of 75 grams of N-benzyloxycarbonyl-4-[ethylenebis(thio)]-L-proline, 150 ml. of methylene chloride, 300 ml. of isobutylene and 3 ml. of concentrated sulfuric acid is sealed in a container and shaken at room temperature for 4 days. The cooled container is opened and the contents of the container diluted with an additional 500 ml. of methylene chloride. The methylene chloride solution is washed with 500 ml. of 5% sodium carbonate solution, 2×250 ml. of water, and then dried over anhydrous magnesium sulfate. The methylene chloride is then concentrated under reduced pressure to yield N-benzyloxycarbonyl-4-[ethylenebis(thio)]-L-proline, tert. butyl ester.

A solution of 25 grams of this ester in 500 ml. of absolute alcohol, to which is added 5 grams of freshly prepared palladium black is stirred at room temperature under positive hydrogen pressure until the evolution of carbon dioxide ceases. The catalyst is removed by filtration and the filtrate concentrated under reduced pressure to yield the desired 4-[ethylenebis(thio)]-L-proline, tert. butyl ester.

(b) 1-(N-Benzyloxycarbonyl-L-alanyl)-4-[ethylenebis(thio)]-L-proline, tert. butyl ester To an ice-cooled solution of N-benzyloxycarbonyl-L-alanine (55 grams) and hydroxybenzotriazole (43 grams) in 476 ml. of tetrahydrofuran there is added 45.8 grams of N,N'-dicyclohexylcarbodiimide over a ten minute period. The reaction mixture is allowed to stir for ninety minutes at room temperature. The precipitated N,N-40-dicyclohexylurea is removed by filtration and 46.8 grams of 4-[ethylenebis(thio)]-L-proline, tert. butyl ester is added to the filtrate. The tetrahydrofuran is removed by distillation under reduced pressure and the residue dissolved in 500 ml. of dimethylformamide to which 50 ml. of triethylamino has been added. The reaction mixture is allowed to stand for sixteen hours at room temperature and then the dimethylformamide removed by distillation under reduced pressure. The residue is dissolved in ethyl acetate and the ethyl acetate solution washed with water, 10% aqueous citric acid and finally be a saturated aqueous sodium bicarbonate solution. The ethyl acetate solution is dried over anhydrous magnesium sulfate and then removed by distillation under reduced pressure to yield 1-(N-benzyloxycarbonyl-L-alanyl)-4-[ethylenebis(thio)]-L-proline, tert. butyl ester.

(c) 1-(L-Alanyl)-4-[ethylenebis(thio)]-L-proline, tert. butyl ester.

A solution of 10 grams of 1-(N-benzyloxycarbonyl -L-alanyl)-4-[ethylenebis(thio)]-L-proline, tert. butyl ester in 150 ml. of absolute ethanol is hydrogenated in the presence of 1.5 grams of freshly prepared palladium black until the evolution of carbon dioxide ceases. The mixture is filtered to remove the catalyst and the filtrate concentrated under reduced pressure to yield 1-(L-alanyl)-4-[ethylenebis(thio)]-L-proline, tert. butyl ester.

(d) 1-[N-(1-(S)-Ethoxycarbonyl-3-phenylpropyl)-L-alanyl]-4-[ethylenebis(thio)]-L-proline To a solution of 410 mg. of 1-(L-alanyl)-4-[ethylenebis(thio)]-L-proline, tert, butyl ester in 10 ml. of tetrahydrofuran there is added 1.4 grams of ethyl 2-oxo-4-phenylbutyrate and 3 grams of molecular sieves. Sodium cyanoborohydride (150 mg.) is added in portions over the course of several hours, and the mixture is stirred at room temperature overnight. After filtration and concentration under vacuum, the residue is treated with 25 ml. of trifluoroacetic acid at room temperature for two hours. After removal of the acid, the product is purified by absorption on ion exchange resin and by gel filtration (LH-20). Concentration and drying of product rich cuts affords the desired 1-[N-(1-(S)-ethoxycarbonyl-3-phenylpropyl)-L-alanyl]-4-[ethylenebis(thio)]-L-proline.

Example 2

1-[N-(1-(S)-Benzyloxycarbonyl-3-phenylpropyl)-L-alanyl[-4-(S)-(phenylthio)-L-proline (a) 4-(S)-(Phenylthio)-L-proline, phenylmethyl ester, hydrochoride salt Six hundred ml. of benzyl alcohol are cooled to 10° and, with vigorous stirring, there is added over the course of 30 minutes, 100 grams of thionyl chloride, while the temperature is maintained at 10°. To this solution there is added, at 10°, 50 grams of cis-4-(phenylthio)-L-proline and the mixture stirred for 48 hours at room temperature. To this reaction mixture there is then added 4 liters of anhydrous ether and the mixture stirred vigorously with cooling. The precipitated solid is filtered, washed with ether and dried to yield the desired 4-(S)-(phenylthio)-L-proline, phenylmethyl ester hydrochloride salt.

The free 4-(S)-(phenylthio)-L-proline, phenylmethyl ester can be obtained by treating the aqueous solution of the hydrochoride with sodium bicarbonate, extracting the liberated ester with ether and concentration of the dried ether solution.

(b) 1-(N-1,1-Dimethylethoxycarbonyl-L-alanyl)-4-(S)-(phenylthio)-L-proline, phenylmethyl ester A solution of 11.7 grams of tert. butyloxycarbonyl-L-alanine in 500 ml. of acetonitrile is cooled to −20° and 6.8 ml. of N-methylmorpholine is added, followed by 8.1 ml. of isobutyl chloroformate. The reaction mixture is allowed to stir for 5 minutes at −20° and a solution of 17.4 grams of 4-(S)-(phenylthio)-L-proline, phenylmethyl ester, hydrochloride salt and 6.8 ml. of N-methylmorpholine in 500 ml. of chloroform is added. The reaction mixture is allowed to warm slowly to room temperature, with stirring. After 18 hours, the reaction mixture is filtered and the filtrate concentrated under reduced pressure. The residue is partitioned between ethyl acetate and water. The ethyl acetate layer is then washed with 0.2 N aqueous hydrochloric acid, water, saturated sodium bicarbonate solution, and saturted sodium chloride solution. The ethyl acetate layer is dried over anhydrous magnesium sulfate and concentrated under reduced pressure to yield the desired 1-(N-1,1-dimethylethoxycarbonyl-L-alanyl)-4-(S)-(phenylthio)-L-proline, phenylmethyl ester.

(c) 1-(L-Alanyl)-4-(S)-(phenylthio)-L-proline, phenylmethyl ester

A solution of 7.5 grams of 1-(N-1,1-dimethylethoxycarbonyl-L-alanyl)-4-(S)-(phenylthio)-L-proline, phenylmethyl ester in 250 ml. of ethyl acetate is saturated with hydrogen chloride. After two hours at room temperature the solvent is evaporated under reduced pressure and the residue kept in a desiccator over sodium hydroxide pellets.

(d) 1-(L-Alanyl)-4-(S)-(phenylthio)-L-proline

To a solution of 5.0 grams of 1-(L-alanyl)-4-(S)-(phenylthio)-L-proline, phenylmethyl ester in 200 ml. of aqueous ethanol there is added 1 gram of freshly prepared palladium black and the mixture is hydrogenated at 50 psi of hydrogen. The reaction mixture is filtered and concentrated under reduced pressure to yield the desired (S)-1-(L-alanyl)-4-(phenylthio)-L-proline.

(e) 1-[N-(1-Benzyloxycarbonyl-3-phenylpropyl)-L-alanyl]-4-(S)-(phenylthio)-L-proline A solution of 200 mg. of 1-(L-alanyl)-4-(S)-(phenylthio)-L-proline and 1.1 grams of benzyl 2-oxo-4-phenylbutyrate in 8 ml. of ethanol is stored at room temperature with 3 grams of powdered molecular sieves (type 4A). Over the course of three hours, 75 mg. of sodium cyanoborohydride is added. The reaction mixture is filtered and concentrated under reduced pressure. The residue is purified by absorption on a strong cation exchange resin and elution with 2% pyridine in water. After passage through a gel filtration column, the desired product, 1-[N-(1-benzyloxycarbonyl-3-phenylpropyl)-L-alanyl]-4-(S)-(phenylthio)-L-proline, is obtained as a mixture of isomers that can be separated by high performance liquid chromatography.

EXAMPLE 3

1-[N-(1-(S)-Ethoxycarbonyl-3-phenylpropyl)-L-alanyl]-4-(S)-(phenylmethyl)-L-proline (a) 4-(S)-(Phenylmethyl)-L-proline, phenylmethyl ester, hydrochloride salt Following the procedure of Example 2(a), cis-4-(phenylmethyl)-L-proline is converted to the desired 4-(S)-(phenylmethyl)-L-proline, phenylmethyl ester, hydrochloride salt.

(b) 1-[N-(1,1-Dimethylethoxycarbonyl)-L-alanyl]-4-(S)-(phenylmethyl)-L-proline, phenylmethyl ester A solution of 11.7 grams of tert. butyloxycarbonyl-L-alanine in 500 ml. of acetonitrile is cooled to −20° and 6.8 ml. of N-methylmorpholine is added, followed by 8.1 ml. of isobutyl chloroformate. The reaction mixture is allowed to stir for 5 minutes at −20° and a solution of 15.4 grams of 4-(S)-(phenylmethyl)-L-proline, phenylmethyl ester, hydrochloride and 6.8 ml. of N-methylmorpholine in 500 ml. of chloroform is added. The reaction mixture is allowed to warm slowly to room temperature, with stirring. After 18 hours the solvent is evaporated under reduced pressure. The oily residue is partitioned between ethyl acetate and water. The ethyl acetate layer is then washed with 0.2 N aqueous hydrochloric acid, water and with saturated aqueous sodium bicarbonate solution. The ethyl acetate layer is dried over anhydrous magnesium sulfate and concentrated under reduced pressure to yield the desired 1-[N-(1,1-dimethylethoxycarboxy)-L-alanyl]-4-(S)-(phenylmethyl)-L-proline, phenylmethyl ester.

(c) 1-(L-Alanyl)-4-(S)-(phenylmethyl)-L-proline, phenylmethyl ester, hydrochloride A solution of 7.5 grams of 1-[N-(1,1-dimethylethoxycarbonyl)-L-alanyl]-4-(S)-(phenylmethyl)-L-proline, phenylmethyl ester in 250 ml. of ethyl acetate is saturated with hydrogen chloride. After two hours the solvent is evaporated under reduced pressure and the residue is kept in a desiccator over sodium hydroxide pellets to yield the desired 1-(L-alanyl-4-(S)-(phenylmethyl)-L-proline, phenylmethyl ester, hydrochloride.

(d) 1-(L-Alanyl)-4-(S)-(phenylmethyl)-L-proline

A solution of 10 grams of 1-(L-alanyl)-4-(S)-(phenylmethyl)-L-proline, phenylmethyl ester (liberated from its hydrochloride salt) in 150 ml. of absolute alcohol is hydrogenated in the presence of 1.5 grams of 10% palladium on carbon until the uptake of hydrogen ceases. The mixture is filtered to remove the catalyst and the filtrate is concentrated under reduced pressure to yield the desired 1-(L-alanyl)-4-(S)-(phenylmethyl)-L-proline.

(e) 1-[N-(1-(S)-Ethoxycarbonyl-3-phenylpropyl)-L-alanyl]-4-(S)-(phenylmethyl)-L-proline A solution of 1-(L-alanyl)-4-(S)-(phenylmethyl)-L-proline and ethyl 2-oxo-4-phenylbutyrate in ethanol is stored at room temperature with powdered molecular sieves. Over the course of several hours, sodium cyanoborohydride is added and the reaction mixture is filtered and concentrated under reduced pressure. The residue is purified by absorption on ion exchange resin to yield 1-[N-(1-(S)-ethoxycarbonyl-3-phenylpropyl)-L-alanyl]-4-(S)-(phenylmethyl)-L-proline.

EXAMPLE 4

1-[N-(1-(S)-Ethoxycarbonyl-3-phenylpropyl)-L-alanyl]-4-(R)-phenyl-L-proline

A mixture of 0.85 grams of 1-(L-alanyl)-4-(R)-phenyl-L-proline [prepared by employing cis-4-phenyl-L-proline in the procedure of Example 2(a) to (d)], 0.2 grams of ethyl 2-oxo-4-phenylbutyrate and 1.5 grams of molecular sieves in 10 ml. of ethanol is hydrogenated under 40 psi with 1 gram of 10% palladium on carbon as the catalyst. The mixture is filtered when the uptake of hydrogen has ceased, and the filtrate is concentrated. The crude product is absorbed on an ion exchange resin (Dowex 50, H+) and eluted with 2% pyridine in water to yield the desired 1-[N-(1-(S)-ethoxycarbonyl-3-phenylpropyl)-L-alanyl]-4-(R)-phenyl-L-proline.

EXAMPLE 5

1-[N-(1-(S)-Ethoxycarbonyl-3-phenylpropyl)-L-alanyl]-4-(S)-(phenylthio)-L-proline Ethyl 2-oxo-4-phenylbutyrate (1.03 gram) and 1-(L-alanyl)-4-(S)-(phenylthio)-L-proline (0.19 gram) are dissolved in a 1:1 ethanol-water solvent. A solution of sodium cyanoborohydride (0.19 gram) in ethanol-water is added dropwise at room temperature over the course of two hours. When the reaction is completed, the product is absorbed in strong acid ion exchange resin and eluted with 2% pyridine water. The product rich cuts are freeze dried and the desired isomer is separated chromatographically to yield 1-[N-(1-(S)-ethoxycarbonyl-3-phenylpropyl)-L-alanyl]-4-(S)-(phenylthio)-L-proline.

EXAMPLE 6

1-[N-(1-Carboxy-2-(S)-benzoylamino-3-phenyl-propyl)-D,L-alanyl]-4-(S)-(phenylmethyl)-L-proline (a) 2-Amino-3-(S)-benzoylamino-4-phenyl butyric acid To a mixture of 2.18 g. of N-phthaloyl-L-2-amino-3-phenylpropionaldehyde [Peterson et al., J.Am. Chem. Soc., Vol. 79, 1389(1957)] and 0.87 g. of potassium metabisulfite in (1:1) watermethanol there is added 0.55 g. of sodium cyanide with vigorous stirring. The mixture is stirred for 1.5 hours, diluted with ethyl acetate and filtered. The organic layer is washed with water and dried (MgSO₄). The solvent is removed in vacuo to yield N-phthaloyl-3-amino-4-phenyl-2-hydroxy butyronitrile.

A solution of this material in anhydrous ethanol that is saturated with anhydrous ammonia is allowed to stand for 3 days at room temperature. The solvent is removed in vacuo. The residue is refluxed for 6 hours in concentrated hydrochloric acid and then evaporated to dryness. The residue is purified on a column of Dowex-50 (H+) ion-exchange resin, eluting in sequence with water-methanol (10:1), water-pyridine (50:1), and finally 0.5 M ammonium hydroxide solution. The desired 2,3-diamino-4-phenyl propionic acid is isolated from this last eluant by concentration to dryness.

A solution of the copper complex of this amino acid is prepared and the 3-amino group is benzoylated in situ with benzoyl chloride under basic conditions as described by Roeske et al., J.Am. Chem. Soc., Vol. 78, p. 5883 (1956). The copper complex is cleaved with hydrogen sulfide and work up is carried out as described by Roeske et al. to yield the desired 2-amino-3-(S)-benzoylamino-4-phenyl butyric acid.

(b) 1-Pyruvoyl-(cis)-4-(phenylmethyl)-L-proline (cis)-4-(Phenylmethyl)-L-proline is converted to its tert butyl ester as set forth in Example 1(a) and treated with pyruvoyl chloride according to the procedure of Hausler et al., Chem. Ber., Vol. 107, p. 145–151 (1974), to yield 1-pyruvoyl-(cis)-4-(phenylmethyl)-L-proline, tert. butyl ester. Treatment with trifluoroacetic acid and anisole yields the desired 1-pyruvoyl-(cis)-4-(phenylmethyl)-L-proline.

(c) 1-[N-(1-Carboxy-2-(S)-benzoylamino-3-phenylpropyl)-D,L-alanyl]-4-(S)-(phenylmethyl)-L-proline A solution of 1-pyruvoyl-(cis)-4-(phenylmethyl)-L-proline, 2-amino-3-(S)-benzoylamino-4-phenyl butyric acid, and sodium cyanoborohydride in methanol is adjusted to neutrality with dilute methanolic sodium hydroxide. After standing at room temperature for several days the product is absorbed on strong acid ion-exchange resin and eluted with 2% pyridine in water to yield 1-[N-(1-carboxy-2-(S)-benzoylamino-3-phenylpropyl)-D,L-alanine]-4-(S)-(phenylmethyl)-L-proline as a mixture of isomers which may be separated by chromatographic methods if desired.

EXAMPLE 7

1-[N-(1-Carbethoxy-2-(S)-benzoylamino-3-phenylpropyl)-D,L-alanyl]-4-(S)-(phenylmethyl)-L-proline 2-Amino-3-(S)-benzoylamino-4-phenylbutyric acid is treated with a saturated solution of hydrogen chloride in absolute ethanol for 4 hours. The solvent is removed in vacuo to yield 2-amino-3-(S)-benzoylamino-4-phenyl butyrate hydrochloride. This intermediate is condensed with 1-pyruvoyl-(cis)-4-(phenylmethyl)-L-proline in the presence of sodium cyanoborohydride as set forth in Example 6 (c) yield 1-[N-(1-carbethoxy-2-(S)-benzoylamino-3-phenylpropyl)-D,L-alanyl]-4-(S)-(phenylmethyl)-L-proline.

EXAMPLE 8

1-[N-(1-Ethoxycarbonyl-3-phenylpropyl)-L-alanyl]-4-[ethylenebis(oxo)]-L-proline A mixture of 3 grams of 1-(L-alanyl)-4-[ethylenebis(oxo)]-L-proline [prepared according to the procedure of Example 2 (a)–(d)], 5 grams of ethyl 2-oxo-4-phenylbutyrate, 15 grams of molecular sieves and 3.5 grams of Raney nickel in 85 ml. of ethanol is hydrogenated at 25° under 40 psi of hydrogen. The mixture is filtered after the hydrogen uptake has ceased and the filtrate is concentrated under reduced pressure. The residue is dissolved in a mixture of water and ehtyl acetate. The pH of the well stirred mixture is adjusted to 8.5 with concentrated aqueous sodium carbonate solution. The organic phase is separated and the aqueous phase is extracted with additional ethyl acetate. The aqueous phase is adjusted to pH 4.25 with concentrated hydrochloric acid, saturated with sodium chloride and extracted several times with ethyl acetate. The combined ethyl acetate extracts are dried over anhydrous magnesium sulfate and concentrated to yield 1-[N-(1-ethoxycarbonyl-3-phenylpropyl)-L-alanyl]-4-[ethylenebis(oxo)]-L-proline.

This product can be converted to a maleic acid salt by treatment of an acetonitrile solution thereof with an acetonitrile solution of an equivalent amount of maleic acid.

EXAMPLES 9-84

Following the procedures of Examples 1 to 5 and 8, the dipeptide shown below in Col. I is coupled with the keto compound shown below in Col. II in the presence of sodium cyanoborohydride or a catalytic reducing agent to yield the product shown below in Col. III.

Col. I $$H_2N-\underset{\underset{R_3}{|}}{CH}-\overset{\overset{O}{\|}}{C}-R_4$$

Col. II $$R-\overset{\overset{O}{\|}}{C}-\underset{\underset{R_1}{|}}{C}=O$$

Col. III

-continued $$R-\overset{\overset{O}{\|}}{C}-\underset{\underset{R_3}{|}}{CH}-NH-\underset{\underset{R_1}{|}}{CH}-\overset{\overset{O}{\|}}{C}-R_4$$

Alternatively, following the procedure of Examples 6 and 7, the amino acid (or ester, amide, or hydroxamic acid) of Col. IV is coupled with the ketone of Col. V in the presence of sodium cyanoborohydride to yield the product shown in Col. III.

Col. IV $$R-\overset{\overset{O}{\|}}{C}-\underset{\underset{R_1}{|}}{CH}-NH_2$$

Col. V $$O=\underset{\underset{R_3}{|}}{C}-\overset{\overset{O}{\|}}{C}-R_4$$

| Example | R4 | R3 | R1 | R |
|---|---|---|---|---|
| 9 | 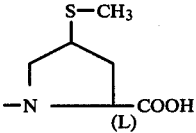 (L) with S—CH3 | —CH3 | —(CH2)2—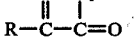 | C2H5O— |
| 10 | 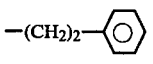 (L) with Cl | —C2H5 | —CH2—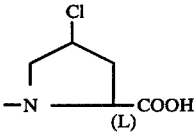 | HO— |
| 11 | 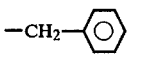 (L) with F | —H | —(CH2)2—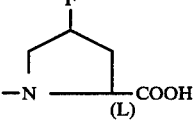 | C2H5O— |
| 12 | 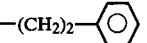 (L) with H3CO, OCH3 | —CH3 | —CH3 | C2H5O— |
| 13 | 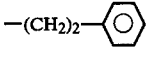 (L) with N3 | —CH3 | —C4H9 | HO— |
| 14 | 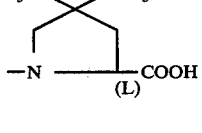 (L) with CH2—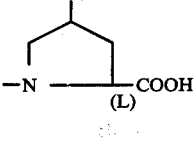—F | —(CH2)4—NH2 | —(CH2)2—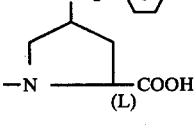 | C2H5O— |
| 15 |  (L) with (CH2)2—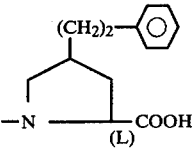 | —CH3 | —(CH2)2—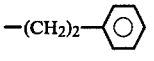 | C2H5O— |

-continued

| Example | R4 | R3 | R1 | R |
|---|---|---|---|---|
| 16 | 4-(2-thienylmethyl)pyrrolidine-2(L)-carboxylic acid | $-CH_3$ | $-(CH_2)_2-C_6H_5$ | HO— |
| 17 | 4-(2-furylmethyl)pyrrolidine-2(L)-carboxylic acid | $-(CH_2)_4-NH_2$ | $-CH_2-C_6H_5$ | HO— |
| 18 | 4-(2-pyridylmethyl)pyrrolidine-2(L)-carboxylic acid | $-CH_3$ | $-(CH_2)_2-C_6H_5$ | $C_2H_5O-$ |
| 19 | 4-cyclohexylpyrrolidine-2(L)-carboxylic acid | $-CH_3$ | $-(CH_2)_2-C_6H_5$ | $C_2H_5O$ |
| 20 | 4-(cyclohexylmethyl)pyrrolidine-2(L)-carboxylic acid | $-(CH_2)_4-NH_2$ | $-(CH_2)_3-C_6H_5$ | HO— |
| 21 | 4-(carbamoyloxy)pyrrolidine-2(L)-carboxylic acid | $-CH_3$ | $-(CH_2)_2-C_6H_5$ | $C_2H_5O$ |
| 22 | 4-(N,N-dimethylcarbamoyloxy)pyrrolidine-2(L)-carboxylic acid | $-CH_3$ | $-(CH_2)_2-C_6H_5$ | $C_2H_5O-$ |
| 23 | 4-(4-fluorophenoxy)pyrrolidine-2(L)-carboxylic acid | $-CH_3$ | $-(CH_2)_2-C_6H_5$ | $C_2H_5O-$ |

-continued

| Example | R₄ | R₃ | R₁ | R |
|---|---|---|---|---|
| 24 | 4-(4-methylbenzyloxy)-pyrrolidine-2-carboxylic acid (L), R₄ = –O–CH₂–C₆H₄–CH₃ on pyrrolidine | –CH₃ | –(CH₂)₂–C₆H₅ | C₂H₅O– |
| 25 | 4-(2-phenylethoxy)-pyrrolidine-2-carboxylic acid (L), R₄ = –O–(CH₂)₂–C₆H₅ on pyrrolidine | –(CH₂)–NH₂ | –(CH₂)₂–C₆H₅ | HO– |
| 26 | 4-(naphth-2-yloxy)-pyrrolidine-2-carboxylic acid, R₄ = –O–(2-naphthyl) on pyrrolidine | –CH₃ | –(CH₂)₂–C₆H₅ | C₂H₅O– |
| 27 | 4-(biphenyl-4-yloxy)-pyrrolidine-2-carboxylic acid, R₄ = –O–C₆H₄–C₆H₅ on pyrrolidine | –CH₃ | –(CH₂)₂–C₆H₅ | C₂H₅O– |
| 28 | 4-(benzylthio)-pyrrolidine-2-carboxylic acid (L), R₄ = –S–CH₂–C₆H₅ on pyrrolidine | –CH₃ | –(CH₂)₂–C₆H₅ | HO– |
| 29 | 4-(phenylthio)-pyrrolidine-2-carboxylic acid (L), R₄ = –S–C₆H₅ on pyrrolidine | –CH₃ | –(CH₂)₂–C₆H₅ | C₂H₅O– |
| 30 | 4-(4-methoxyphenylthio)-pyrrolidine-2-carboxylic acid (L), R₄ = –S–C₆H₄–OCH₃ on pyrrolidine | –CH₃ | –(CH₂)₂–C₆H₅ | C₂H₅O– |
| 31 | 4-(naphth-2-ylthio)-pyrrolidine-2-carboxylic acid (L), R₄ = –S–(2-naphthyl) on pyrrolidine | –CH₃ | –(CH₂)₂–C₆H₅ | C₂H₅O– |
| 32 | 3-chloro-pyrrolidine-2-carboxylic acid (L), R₄ = –Cl on pyrrolidine | –CH₃ | –(CH₂)₂–C₆H₅ | HO– |

-continued

| Example | R₄ | R₃ | R₁ | R |
|---|---|---|---|---|
| 33 | 3-(benzoylamino)pyrrolidine-2-carboxylic acid (L) | —CH₃ | —(CH₂)₂—C₆H₅ | HO— |
| 34 | 3-(4-fluorophenylthio)pyrrolidine-2-carboxylic acid (L) | —CH₃ | —(CH₂)₂—C₆H₅ | C₂H₅O— |
| 35 | 3-(2-naphthyloxy)pyrrolidine-2-carboxylic acid (L) | —CH₃ | —(CH₂)₂—C₆H₅ | C₂H₅O |
| 36 | 3-(benzyloxy)pyrrolidine-2-carboxylic acid (L) | —CH₃ | —(CH₂)₂—C₆H₅ | C₂H₅O— |
| 37 | 3-(4-fluorophenoxy)pyrrolidine-2-carboxylic acid (L) | —CH₃ | —(CH₂)₂—C₆H₅ | C₂H₅O |
| 38 | 3-(methylthio)pyrrolidine-2-carboxylic acid (L) | —CH₃ | —(CH₂)₂—C₆H₅ | C₂H₅O— |
| 39 | 3-(phenylthio)pyrrolidine-2-carboxylic acid (L) | —CH₃ | —(CH₂)₂—C₆H₅ | C₂H₅O— |
| 40 | 3-(benzylthio)pyrrolidine-2-carboxylic acid (L) | —CH₃ | —(CH₂)₂—C₆H₅ | C₂H₅O— |
| 41 | 3-(acetylamino)pyrrolidine-2-carboxylic acid (L) | —CH₃ | —(CH₂)₂—C₆H₅ | C₂H₅O— |
| 42 | 2-(4-hydroxyphenyl)pyrrolidine-2-carboxylic acid (L) | —CH₃ | —(CH₂)₂—C₆H₅ | C₂H₅O— |
| 43 | 2-phenylpyrrolidine-2-carboxylic acid (L) | —CH₃ | —(CH₂)₂—C₆H₅ | HO— |

-continued

| Example | R₄ | R₃ | R₁ | R |
|---|---|---|---|---|
| 44 | 4,4-dichloro-pyrrolidine-2-COOH (L) | —CH₃ | —(CH₂)₂—C₆H₅ | HO— |
| 45 | 4,4-difluoro-pyrrolidine-2-COOH (L) | —CH₃ | —(CH₂)₂—C₆H₅ | C₂H₅O— |
| 46 | 4,4-dimethoxy-pyrrolidine-2-COOH (L) | —CH₃ | —(CH₂)₂—C₆H₅ | C₂H₅O— |
| 47 | 1,5-dioxa-8-azaspiro[5.4] pyrrolidine-2-COOH (L) | —CH₃ | —(CH₂)₂—C₆H₅ | C₂H₅O— |
| 48 | 2,2-dimethyl-1,3-dioxolane-pyrrolidine-COOH (L) | —CH₃ | —(CH₂)₂—C₆H₅ | HO— |
| 49 | 4,4-(isopropylidenedioxy)-pyrrolidine-2-COOH (L) | —CH₃ | —(CH₂)₂—C₆H₅ | C₂H₅O— |
| 50 | 1,5-dithia-8-azaspiro pyrrolidine-2-COOH (L) | —CH₃ | —(CH₂)₂—C₆H₅ | C₂H₅O— |
| 51 | methyl-dithiolane-pyrrolidine-2-COOH (L) | —CH₃ | —(CH₂)₂—C₆H₅ | C₂H₅O— |
| 52 | 4-phenylthio-pyrrolidine-2-COOH (L) | —CH₃ | —CH₃ | HO— |

-continued

| Example | R₄ | R₃ | R₁ | R |
|---|---|---|---|---|
| 53 | L-4-benzyl-pyrrolidine-2-COOH | —CH₃ | —CH(CH₃)₂ | HO— |
| 54 | L-3-phenyl-pyrrolidine-2-COOH | —CH₃ | —CH₂—COOH | HO— |
| 55 | L-4-(4-fluorophenoxy)-pyrrolidine-2-COOH | —CH₃ | —(CH₂)₂—S—CH₃ | HO— |
| 56 | L-3-phenyl-pyrrolidine-2-COOH | —CH₃ | —CH₂-(indol-3-yl) | H₃CO— |
| 57 | L-3-phenoxy-pyrrolidine-2-COOH | —H | —(CH₂)₂—C₆H₅ | HO— |
| 58 | L-5-(2-hydroxyphenyl)-pyrrolidine-2-COOH | —CH₃ | —H | HO— |
| 59 | L-4-(phenylthio)-pyrrolidine-2-COOH | —(CH₂)₂—S—CH₃ | —(CH₂)₂—C₆H₅ | HO— |
| 60 | L-4-benzyl-pyrrolidine-2-COOH | —CF₃ | —(CH₂)₂—C₆H₅ | HO— |
| 61 | L-4-(2-phenylethoxy)-pyrrolidine-2-COOH | —CH₂OH | —(CH₂)₂—C₆H₅ | HO— |

-continued
| Example | R₄ | R₃ | R₁ | R |
|---|---|---|---|---|
| 62 | 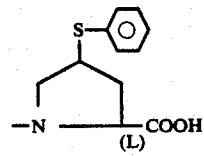 | -CH₂-(indole) | -(CH₂)₂-Ph | H₃CO— |
| 63 | 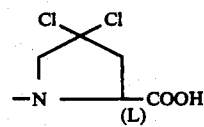 | -CH₂-(imidazole) | -(CH₂)₂-Ph | HO— |
| 64 | 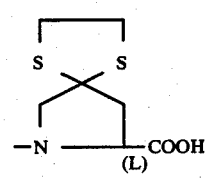 | -(CH₂)₃NHC(=NH)NH₂ | -(CH₂)₂-Ph | HO— |
| 65 | 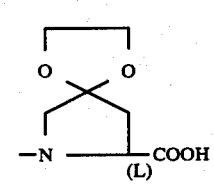 | -CH₂-Ph | -(CH₂)₂-Ph | HO— |
| 66 | 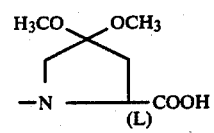 | -CH₂SH | -(CH₂)₂-Ph | HO— |
| 67 | 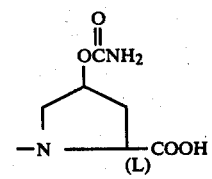 | -(CH₂)₂S-CH₃ | -(CH₂)₂-Ph | HO— |
| 68 | 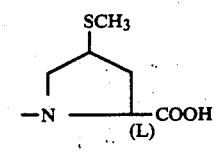 | -CH₂NH-C(=O)-Ph | -(CH₂)₂-Ph | HO— |
| 69 | 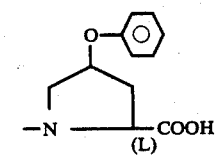 | -CH₂N(CH₃)₂ | -(CH₂)₂-Ph | HO— |
| 70 | 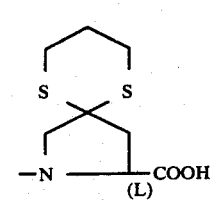 | -CH₂NH-C(=O)-Ph | -(CH₂)₂-Ph | HO— |

-continued

| Example | R₄ | R₃ | R₁ | R |
|---|---|---|---|---|
| 71 | pyrrolidine with 4-O-biphenyl, COOH (L) | $-CH_2NH-\underset{O}{\overset{\parallel}{C}}-CH_3$ | $-(CH_2)_2-C_6H_5$ | HO— |
| 72 | pyrrolidine with 4-S-phenyl, COOH (L) | $-CH_3$ | $-(CH_2)_2-C_6H_5$ | $(H_3C)_2NC_2H_5$ |
| 73 | pyrrolidine with 4-O-(4-Cl-phenyl), COOH (L) | $-CH_3$ | $-(CH_2)_2-C_6H_5$ | $H_3C-\underset{O}{\overset{\parallel}{C}}-NH-C_2H_5O$ |
| 74 | pyrrolidine with 4-CH₂-phenyl, COOH (L) | $-CH_3$ | $-(CH_2)_2-C_6H_5$ | $C_6H_5-CH_2-O-$ |
| 75 | pyrrolidine with 4-CH₂-(4-OCH₃-phenyl), COOH (L) | $-CH_3$ | $-(CH_2)_2-C_6H_5$ | HO—NH— |
| 76 | pyrrolidine with 3-S-CH₃, COOH (L) | $-CH_3$ | $-(CH_2)_2-C_6H_5$ | $(H_3C)_2N-$ |
| 77 | pyrrolidine with 4-S-phenyl, COOH (L) | $-CH_3$ | $-CH(CH_2C_6H_5)NHC(O)C_6H_5$ | HO— |
| 78 | pyrrolidine with 4,4-dithiolane spiro, COOH (L) | $-CH_3$ | $-CH(CH_2C_6H_5)NHC(O)C_6H_5$ | $H_5C_2O-$ |
| 79 | pyrrolidine with 4-CH₂-phenyl, COOH (L) | $-CH_3$ | $-CH((CH_2)_2C_6H_5)NHC(O)C_6H_5$ | HO— |

-continued

| Example | $R_4$ | $R_3$ | $R_1$ | $R$ |
|---|---|---|---|---|
| 80 | (L)-4-(4-fluorophenoxy)proline | $-CH_3$ | $-CH((CH_2)_3-C_6H_5)(NH-CO-C_6H_4-OCH_3)$ | $HO-$ |
| 81 | (L)-4-(phenylthio)proline | $-CH_3$ | $-CH(CH_2-C_6H_{11})(NH-CO-C_6H_5)$ | $H_5C_2O-$ |
| 82 | (L)-4-phenylproline | $-CH_3$ | $-CH(CH_2-CH(CH_3)_2)(NH-CO-C_6H_5)$ | $HO-$ |
| 83 | (L)-4-cyclohexylproline | $-CH_3$ | $-CH(C_6H_5)(NH-CO-C_6H_5)$ | $HO-$ |
| 84 | (L)-4-(phenylthio)proline | $-CH_3$ | $-CH(CH_2-C_6H_4-OCH_3)(NH-CO-C_6H_5)$ | $HO-$ |

The products of Examples 12, 46 and 66 can be converted to the corresponding 4-ketoproline product by treatment of the 4-dimethoxyproline product with an acid such as hydrochloric acid, p-toluenesulfonic acid, or 88% formic acid as the last step of the synthetic procedure.

In preparing the products of Examples 14, 17, 20 and 25 the free $NH_2$ group ($R_3$ substituent) is protected, for example, by a t-butoxycarbonyl group during the coupling reaction and this protecting group is then removed, for example, by treatment with trifluoroacetic acid and anisole or 88% formic acid as the last step of the synthetic procedure.

Similarly, in preparing the product of Example 66, the free SH group ($R_3$ substituent) would be protected, for example, as the S-acetyl during the coupling and then converting by hydrolysis or ammonolysis to the mercaptan as the last step of the synthetic procedure.

EXAMPLE 85

1-[N-(1-Carboxyethyl)-L-alanyl]-4-(S)-(phenylmethyl)-L-proline (a) N-(1-Carboenzyloxyethyl)-L-alanine 45 grams of benzyl pyruvate and 4.5 grams of L-alanine are dissolved in a mixture of 115 ml. of water and 250 ml. of p-dioxane. The pH is adjusted to 5.5 by the addition of sodium hydroxide. 9.4 grams of sodium cyanoborohydride are added and the mixture is stirred at room temperature for six days. The pH of the mixture is adjusted to 1.0 by the addition of concentrated hydrochloric acid.

This solution is charged to a column of Dowex 50 ($H^+$) prepared in 50 % dioxane-water. The column is washed with 50% dioxane-water, then water, and the product is eluted with 2% pyridine in water. The product fractions are combined and concentrated to dryness in vacuo. The solid residue is triturated with water, filtered, washed with water, and dried to yield 6.8 g. of N-(1-carbobenzyloxyethyl)-L-alanine as a mixture of diastereoisomers.

(b) 1-[N-(1-Carboxyethyl)-L-alanyl]-4-(S)-phenyl methyl)-L-proline 208 mg. of the N-(1-carbobenzyloxyethyl)-L-alanine and 230 mg. of 4-(S)phenylmethyl-L-proline, benzyl ester, hydrochloride are dissolved in dry dimethylformamide. The mixture is cooled to 0° and 0.193 ml. of diphenylphosphoryl azide dissolved in dimethylformamide is added. While the mixture is kept at 0°, a solution of 0.24 ml. of triethylamine in dimethylformamide is added dropwise over ten minutes. The resulting mixture is stirred for three hours at 0° and then stirred overnight at room temperature. The mixture is then diluted with ethyl acetate, washed with water and 5% sodium dicarbonate, and concentrated in vacuo to a small volume. The crude dibenzyl ester product is purified by chromatography (silica gel).

The purified dibenzyl ester product (135 mg.) is dissolved in a mixture of water and methanol. 50 mg. of freshly prepared palladium black are added and the mixture is hydrogenated at 40 psi of hydrogen at room temperature. The reaction mixture is filtered, concentrated in vacuo, and freeze dried to yield 1-[N-(1-carboxyethyl)-L-alanyl]-4-(S)-(phenylmethyl)-L-proline as a mixture of diastereoisomers.

In an analogus manner, the above procedure can be employed to prepare the compounds of Examples 1 to 84.

EXAMPLE 86

1-[N-Carboxy-1-methylethyl)-L-alanyl]-4-[ethylenebis(thio)]-L-proline 7.7 g. of 2-bromoisobutyric acid, benzyl ester, 2.4 g. of 1-(L-alanyl)-4-[ethylenebis(thio)]-L-proline, tert. butyl ester, and 7.0 g. of silver oxide are combined in 40 ml. of benzene. The mixture is refluxed for twenty four hours, than an additional 7.7 g. of the 2-bromoisobutyric acid, benzyl ester and 7.0 g. of silver oxide are added and the refluxing is continued for an additional twenty four hours. The mixture is then cooled, filtered, the solvent is stripped off, and the residue is treated chromatographically to isolate the diester product. This product is treated with trifluoroacetic acid to remove the tert. Butyl ester group and then catalytically hydrogenated to remove the benzyl ester group and yield the desired 1-[N-(1-carboxy-1-methylethyl)-L-alanyl]-4-[ethylenebis(thio)]-L-proline.

EXAMPLES 87–94

Following the procedure of Example 86, the bromo acid shown below in Col. 1 is reacted with the dipeptide ester shown below in Col. II to yield the diester product of Col. III. Removal of the ester groups yields the corresponding free acid.

Col. I

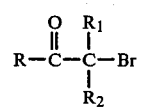

Col. II

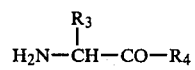

Col. III

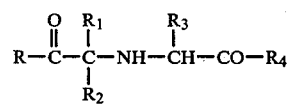

| Example | R | $R_1$ | $R_2$ | $R_3$ | $R_4$ |
|---|---|---|---|---|---|
| 87 | ⌬—CH$_2$— | —CH$_3$ | —CH$_3$ | —CH$_3$ | —N⌐⌐COOC(CH$_3$)$_3$ (L), with S—⌬ substituent |
| 88 | ⌬—CH$_2$— | —(CH$_2$)$_2$—⌬ | —CH$_3$ | —CH$_3$ | —N⌐⌐COOC(CH$_3$)$_3$ (L), with CH$_2$—⌬ substituent |
| 89 | ⌬—CH$_2$— | —CH$_3$ | —CH$_3$ | —(CH$_2$)$_4$NH$_2$ | —N⌐⌐COOC(CH$_3$)$_3$ (L), with ⌬ substituent |
| 90 | ⌬—CH$_2$— | —CH$_3$ | H | —CH$_3$ | —N⌐⌐COOC(CH$_3$)$_3$ (L), with O—⌬ substituent |

-continued

| Example | R | $R_1$ | $R_2$ | $R_3$ | $R_4$ |
|---|---|---|---|---|---|
| 91 | C6H5-CH2- | -CH3 | -C2H5 | -CH3 | -N with ring containing C(O)(O) ketal, -COOC(CH3)3 (L) |
| 92 | C6H5-CH2- | -CH3 | -CH3 | -CH3 | -N with ring bearing -S-C6H4-F substituent, -COOC(CH3)3 (L) |
| 93 | C6H5-CH2- | -CH3 | -CH3 | -CH3 | -N with ring bearing -O-C6H4-F substituent, -COOC(CH3)3 (L) |
| 94 | C6H5-CH2- | -CH3 | -CH3 | -CH3 | -N with ring bearing 2-hydroxyphenyl substituent, -COOC(CH3)3 (L) |

Again, in Example 89, the free NH2 group in the $R_3$ substituent would be protected with a group such as t-butoxycarbonyl which would then be removed as the last step of the synthetic procedure.

EXAMPLE 95

[1(S),4S]-1-[N-(1-Carboxy-3-phenylpropyl)-L-alanyl]-4-(phenylthio)-L-proline (a) Benzyloxycarbonyl-L-alanine, t-butyl ester A mixture of benzyloxycarbonyl-L-alanine (160 g., 0.72 mole), anhydrous dichloromethane (270 ml.), condensed isobutylene (700 ml.), and concentrated sulfuric acid (7.5 ml.) is shaken in a Parr apparatus at room temperature for 3 days. The isobutylene is allowed to evaporate at room temperature overnight and the residue is dissolved in 1 l. of ether. The resulting solution is washed with 1N sodium bicarbonate and brine. After drying over anhydrous MgSO4, the solvent is removed at reduced pressure to give 195 g. of benzyloxy-L-alanine, t-butyl ester as a yellow oil which is used without further purification.

(b) L-Alanine, t-butyl ester, hydrochloride

The crude benzyloxycarbonyl-L-alanine, t-butyl ester (107 g.) is dissolved in 800 ml. of absolute ethanol and the turbid solution is filtered through celite. To the resulting clear filtrate, 383 ml. of 1N hydrochloric acid/ethanol and 10 g. of palladium on carbon catalyst are added. The resulting mixture is hydrogenated (1 atm.) at room temperature overnight. The catalyst is removed by filtration through celite and the solvent is removed at reduced pressure. Addition of ether results in the formation of a colorless solid. Filtration, washing with ether, and drying under vacuum gives 54.25 g. of L-alanine, t-butyl ester, hydrochloride as a colorless solid; m.p. 164°–165° (dec.); $[\alpha]_D^{23} = +2.34°$ (c=2.2, methanol).

(c) N-[1(S)-Ethoxycarbonyl-3-phenylpropyl]-L-alanine, t-butyl ester

To a solution of L-alanine, t-butyl ester, hydrochloride (4.86 g., 26.7 mmole) in 35 ml. of absolute ethanol, there is added 4.2 ml. (6.72 mmole) of 1.6 N sodium ethoxide/ethanol. To the resulting milky solution which is approximately pH 7.5, is added a solution of ethyl 2-oxo-4-phenylbutyrate [prepared by treating ethyl 2-hydroxy-4-phenylbutyrate with oxalyl chloride] (27.6 g.,0.135 mmole) in 25 ml. of ethanol followed by 22 g. of powdered 3A° molecular sieves. The resulting mixture is stirred at room temperature and during the next 30 minutes a total of 4.8 ml. (7.68 mmole) of 1.6 N sodium ethoxide/ethanol is added to maintain a pH of between 6 and 7. After stirring for an additional 30 minutes, a solution of sodium cyanoborohydride (3.35 g., 53.5 mmole) in 20 ml. of ethanol is added over a period of six hours. After stirring for 40 hours, the mixture is filtered through celite and then evaporated at reduced pressure. The residue is dissolved in 350 ml. of ether and the resulting solution is washed with water (3×100 ml.) and then extracted with 1N hydrochloric acid (3×100 ml.). The hydrochloric acid extracts are combined and washed with ether and basified with 4N sodium hydroxide (70 ml.) followed by 1N sodium bicarbonate. The resulting mixture is extracted with ether (2×350 ml.). The ether fractions are combined, washed with water and brine, and dried (MgSO4). The solvent is removed at reduced pressure to give crude product as a mixture of diastereomers $R_f$=0.46 (undesired isomer) and 0.36 (desired isomer), silica gel, petroleum ether: ether, 1:1). The crude material is then filtered through a column of silica gel (petroleum ether:ether, 3:1). Chromatography (silica gel, hexane:ethyl acetate, 92:8) yields N-[1(S)-ethoxycarbonyl-3-phenylpropyl]-L-alanine, t-butyl ester as a colorless oil. $R_f$=0.36 (silica gel, petroleum ether:ether, 1:1).

(d) N-[1(S)-Ethoxycarbonyl-3-phenylpropyl]-L-alanine

A solution of the t-butyl ester product from part (c) (2.54 g., 7.57 mmole) in 25 ml. of trifluoroacetic acid is stirred at room temperature for 3 hours. The trifluoroacetic acid is then removed at reduced pressure. Benzene is added and the solvent is again removed at reduced pressure. The residue is applied to an AG50W-X2 (H+) column (bed volume of 75 ml.). After washing with water, the column is eluted with aqueous pyridine (3%) and 23 ml. fractions are collected. Fractions 12–20 containing the product are combined and lyophilized to give 1.63 g. of N-[1(S)-ethoxycarbonyl-3-phenylpropyl]-L-alanine as a while solid; $\alpha_D^{20} = +26.1°$ (c=1.50, methanol); $R_f=0.28$ (silica gel, chloroform: methanol:acetate acid, 10:1:1).

(e) cis-4-Phenylthio-L-proline, methyl ester, hydrochloride

To 60 ml. of cold methanol (−20°) under argon is added 3.2 ml. (45 mmole) of acetyl chloride. After stirring at −20° for 3 hours, 5.0 g. (22 mmole) of cis-4-phenylthio-L-proline [can be prepared according to the procedure set forth by Ondetti et al. in Example 44 of U.K. patent application No. 2,028,327] is added followed by the dropwise addition of thionyl chloride (1.63 ml., 22 mmole). After stirring for 3 hours at −20°, the cold bath is removed and the mixture is stirred at room temperature overnight. The solvent is then removed at reduced pressure and the residue partitioned between 1N sodium bicarbonate and water and then dried ($Na_2SO_4$). The resulting solution is treated with excess methanolic hydrochloric acid and then concentrated at reduced pressure. Recrystallization from methanol/ether gives 1.89 g. of cis-4-phenylthio-L-proline, methyl ester, hydrochloride as a colorless solid; m.p. 87°–89°; $[\alpha]_D^{20} = 3.7°$ (c=2.05, methanol).

(f) [1(S),4S]-1-[N-(1-Ethoxycarbonyl-3-phenylpropyl)-L-alanyl]-4-(phenylthio)-L-proline, methyl ester To a cold (0°) solution of N-[1(S)-ethoxycarbonyl-3-phenylpropyl]-L-alanine (500 mg., 1.79 mmole) and cis-4-phenylthio-L-proline, methyl ester, hydrochloride (540 mg., 1.1 eq.) in 8 ml. of dimethylformamide under argon is added dropwise 0.43 ml. (1.1 eq.) of diphenylphosphoryl azide. After stirring for several minutes, a solution of triethylamine (0.55 ml., 2.2 eq.) in 1.5 ml. of dimethylformamide is added dropwise over 10 minutes. After stirring for 3 hours, the cold bath is removed and the mixture is stirred at room temperature for 19 hours. The resulting mixture is diluted with ethyl acetate and washed successively with 1N sodium bicarbonate, water (two times), 1N sodium bicarbonate, and brine. After drying over anhydrous $MgSO_4$, the solvent is removed at reduced pressure and the residue chromatographed (silica gel, ethyl acetate:acetone:dichloromethane, 35:5:60) to give 0.55 g. of [1(S),4S]-1-[N-(1-ethoxycarbonyl-3-phenylpropyl)-L-alanyl]-4-(phenylthio)-L-proline, methyl ester as a pale yellow oil; $R_f=0.37$ (silica gel, ethyl acetate).

(g) [1(S),4S]-1-[N-(1-Carboxy-3-phenylpropyl)-L-alanyl]-4-(phenylthio)-L-proline To a solution of [1(S),4S]-1-[N-(1-ethoxycarbonyl-3-phenylpropyl)-L-alanyl]-4-(phenylthio)-L-proline, methyl ester (550 mg., 1.10 mmole) in 7 ml. of ethanol under argon is added 1N sodium hydroxide (2.4 ml., 2.2 eq.). After stirring at room temperature for 4 hours, the solvent is removed at reduced pressure and the residue is applied to an AG50W-X2(H+) column (bed volume of 30 ml.). After washing with water, the column is eluted with aqueous pyridine (3%) and 7 ml. fractions are collected. Fractions 10–14 containing the product are combined and lyophilized to give 455 mg. of [1(S),4S]-1-[N-(1-carboxy-3-phenylpropyl)-L-alanyl]-4-(phenylthio)-L-proline as a white solid; $[\alpha]_D^{20} = -2.7°$ (c=1,methanol); $R_f=0.56$, 0.22 (trace), silica gel (n-butanol:acetic acid:water, 4:1:1), visualized with UV and char (solution prepared by diluting 20 g. of $(NH_4)_2SO_4$ to 100 ml. with water and adding 4 ml. of conc. $H_2SO_4$).

Anal. calc'd. for $C_{24}H_{28}N_2O_5S \cdot 0.25 H_2O$: C, 62.52; H, 6.23; N, 6.07; S, 6.95. Found: C, 62.96; H, 6.09, N, 6.34; S, 6.87.

IR (KBr): 3420, 1710, 1650, 740, 695 $cm^{-1}$.

NMR (60 MHz, DMSO-$d_6$): 1.15 (3H, d, J=6.7 Hz), 7.20(5H,S, aromatic), 7.35 (5H,S, aromatic).

EXAMPLE 96

(S,S)-1-[N-(1-Carboxy-3-phenylpropyl)-L-alanyl]-4-(4-fluorophenoxy)-L-proline

(a) cis-4-(4-Fluorophenoxy)-L-proline, methyl ester, hydrochloride

To a stirred suspension of cis-4-(4-fluorophenoxy)-L-proline (which can be prepared as set forth by Ondetti et al. in Example 36 of U.K. patent application No. 2,028,327) (250 mg., 11 mmole) in 70 ml. of methanol at −30° under argon, there is added 8.09 ml. (10 eq.) of thionyl chloride. After stirring at −20° for 2 hours, the cold bath is removed and the mixture is stirred at room temperature for 16 hours. The solvent is removed at reduced pressure and the residue is dissolved in 150 ml. of dichloromethane. The resulting solution is washed with 1N sodium bicarbonate (twice) and water. After drying ($MgSO_4$), the solution is treated with excess hydrochloric acid and then concentrated at reduced pressure. Recrystallization from methanol/ether gives 1.49 g. of product. The mother liquors yield an additional 0.5 g. of product so that a total of 1.99 g. of cis-4-(4-fluorophenoxy)-L-proline, methyl ester, hydrochloride is obtained; m.p. 147°–148° (s. 144°); $[\alpha]_D^{20} = +6.96°$ (c=1.55, methanol).

(b) (S,S)-1-[N-(1-Ethoxycarbonyl-3-phenylpropyl)-L-alanyl]-4-(4-fluorophenoxy)-L-proline, methyl ester cis-4-(4-Fluorophenoxy)-L-proline, methyl ester, hydrochloride (651 mg., 1.1 eq.) and N-[1-(S)-ethoxycarbonyl-3-phenylpropyl]-L-alanine (600 mg., 2.14 mmole) are reacted according to the procedure of Example 95(f) to yield 600 mg. of (S,S)-1-[N-(1-ethoxycarbonyl-3-phenylpropyl)-L-alanyl]-4-(4-fluorophenoxy)-L-proline, methyl ester as a pale yellow oil; $R_f=0.32$ (silica gel, acetone:ethyl acetate:dichloromethane, 1.5:2.5:6).

(S,S)-1-[N-(1-Carboxy-3-phenylpropyl)-L-alanyl]-4-(4-fluorophenoxy)-L-proline A solution of (S,S)-1-[N-(1-ethoxycarbonyl-3-phenylpropyl)-L-alanyl]-4-(4-fluorophenoxy)-L-proline, methyl ester (600 mg., 1.19 mmole) in 7 ml. of ethanol is treated with 1N sodium hydroxide and worked up according to the procedure of Example 95 (g), to yield 470 mg. of (S,S)-1-[N-(1-carboxy-3-phenylpropyl)-L- alanyl]-4-(4-fluorophenoxy)-L-proline; $[\alpha]_D^{20}= +4.36°$ (c=1.05, methanol); $R_f=0.20$, silica gel (ethyl acetate:-pyridine:acetic acid: water, 60:20:6:11), visualized with UV and char.

Anal. calc'd. for $C_{24}H_{27}N_2O_6F.0.25H_2O$: C, 62.26; H, 5.98; N, 6.05; F, 4.10 Found: C, 62.35; H, 5.98; N, 6.23; F, 4.03.

IR(KBr): 3420, 1720, 1650, 1500, 1200 cm$^{-1}$.

NMR (60 MHz, DMSO-d$_6$): 1.23 (3H, d, J=6.7 Hz), 6.90–7.35 (9H, M, aromatic).

EXAMPLE 97

[1(S),4R]-1-[N-(1-Carboxy-3-phenylpropyl)-L-alanyl]-4-(phenylthio)-L-proline (a) trans-4-Phenylthio-L-proline, hydrochloride Sodium metal (1.9 g., 0.083 g.atom) is dissolved in 90 ml. of ethanol. To this is added with stirring 8.4 ml. (0.082 mole) of phenylmercaptan, followed by 17 g. (0.039 mole) of cis-N-carbobenzyloxy-4-tosyloxy-L-proline, methyl ester [Patchett et al., "Studies on Hydroxyproline", JACS, Vol. 79, p. 185–192 (1957)]. After stirring at room temperature for 20 hours, the mixture is added to 300 ml. of dichloromethane and 150 ml. of water and stirred until the solids dissolve. The layers are separated and the aqueous phase is extracted with dichloromethane (2×150 ml., emulsions partly broken up by adding some ethanol and saturated sodium chloride). The combined organic layers are washed with 150 ml. of saturated sodium chloride, dried (MgSO$_4$), and the solvent evaporated to give 17 g. of a partly crystalline residue. The latter is stirred with 50 ml. of ether, cooled in ice water for 1 hour and the solids filtered. Evaporation of the ether filtrate yields 10.9 g. of trans-4-carbobenzyloxy-4-phenylthio-L-proline, ethyl ester.

The trans-N-carbobenzyloxy-4-phenylthio-L-proline, ethyl ester (10.9 g., 0.028 mole) is saponified in 95 ml. of methanol with 22 ml. (0.044 mole) of 2N sodium hydroxide according to the procedure of Ondetti et al. in Example 44 (b) of U.K. patent application No. 2,028,327 to give 10.9 g. of pale yellow viscous oil. The latter is dissolved in 40 ml. of ethanol, treated with 4 ml. of cyclohexylamine, and diluted with 400 ml. of ether. On seeding, 10.7 g. of colorless trans-N-carbobenzyloxy-4-phenylthio-L-proline, cyclohexylamine salt; m.p. 152–154 (s. 148°); $[\alpha]_D^{23}= -9°$ (c=1, methanol); are obtained.

This cyclohexylamine salt (9.5 g.) is suspended in 50 ml. of ethyl acetate, stirred, and treated with 45 ml. of 1N hydrochloric acid. The aqueous phase is extracted with additional ethyl acetate (3×50 ml.). The combined organic layers are dried (MgSO$_4$) and the solvent evaporated to give 8.0 g. of trans-N-carbobenzyloxy-4-phenylthio-L-proline; $R_f=0.67$ (silica gel, dichloromethane:methanol:acetic acid, 90:5:5) visualized with UV.

A stirred solution of 8.0 g. (0.021 mole) of trans-N-carbobenzyloxy-4-phenylthio-L-proline in 125 ml. of glacial acetic acid is treated with 48 ml. of concentrated hydrochloric acid and heated to reflux for 1 hour. The nearly colorless solution is cooled and the bulk of acids removed on a rotary evaporator at 0.2 mm. to give a solid residue. The latter is rubbed under 150 ml. of isopropanol and the evaporation repeated. Finally, the solid is rubbed under 300 ml. of ether, filtered under nitrogen, and dried in vacuo to give 5.4 g. of nearly colorless trans-4-phenylthio-L-proline, hydrochloride; m.p. 181°–184° (dec.), (s. approx. 170°); $[\alpha]_D^{23}= -22°$ (c=1, pyridine; −18° c=0.5, 50% acetic acid).

Anal. calc'd. for $C_{11}H_{13}NO_2S.HCl.0.25H_2O$: C, 49.99; H,5.53; N,5.30; S,12.14; Cl,13.42. Found: C, 50.23; H,5.38; N,5.22; S,12.08; Cl,13.27.

(b) trans-4-Phenylthio-L-proline,methyl ester, hydrochloride

To a stirred solution of trans-4-phenylthio-L-proline, hydrochloride (1.9 g., 7.19 mmole) in 45 ml. of methanol at −30° under argon, there is added 3.14 ml. (6 eq.) of thionyl chloride dropwise over 10 minutes. After stirring at −20° for 2 hours, the mixture is stirred at room temperature for 24 hours. The solvent is removed at reduced pressure and the residue dissolved in 150 ml. of dichloromethane. The resulting solution is washed with 1N sodium bicarbonate (twice) and water. After drying (MgSO$_4$), the solution is treated with excess methanolic hydrochloric acid and then concentrated at reduced pressure. Recrystallization from acetonitrile gives 1.53 g. of colorless, crystalline solid trans-4-phenylthio-L-proline, methyl ester, hydrochloride; m.p. 103°–104°; $[\alpha]_D^{20}= -1.0°$ (c=2.0, methanol).

(c) [1(S),4R]-1-[N-(1-Ethoxycarbonyl-3-phenylpropyl)-L-alanine]-4-(phenylthio)-L-proline, methyl ester N-[1(S)-Ethoxycarbonyl-3-phenylpropyl]-L-alanine (660 mg.,2.36 mmole) and trans-4-phenylthio-L-proline, methyl ester (712 mg., 1.1 eq.) are reacted according to the procedure of Example 95(f) to give 640 mg. of [1(S),4R]-1-[N-(1-ethoxycarbonyl-3-phenylpropyl)-L-alanine]-4-(phenylthio)-L-proline, methyl ester as a pale yellow oil; $R_f=0.35$ (silica gel, ethyl acetate.

(d) [1(S),4R]-1-[N-(1-Carboxy-3-phenylpropyl)-L-alanyl]-4-(phenylthio)-L-proline A solution of [1(S),4R]-1-[N-(1-ethoxycarbonyl-3-phenylpropyl)-L-alanine]-4-(phenylthio)-L-proline, methyl ester (640 mg., 1.37 mmole) in 8 ml. of ethanol is treated with 1N sodium hydroxide and worked up according to the procedure of Example 95 (g) to yield 492 mg. of [1(S),4R]-1-[N-(1-carboxy-3-phenylpropyl)-L-alanyl]-4-(phenylthio)-L-proline; $[\alpha]_D^{20}= +2.95°$ (c=1.05, methanol; $R_f=0.19$, origin (trace), 0.57 (trace), silica gel (ethyl acetate: pyridine:acetic acid:water, 60:20:6:11) visualized with UV and char.

Anal. calc'd. for $C_{24}H_{28}N_2O_5S.0.5\ H_2O$:

C, 61.92; H, 6.28; N, 6.02; S, 6.89.

Found: C, 62.06; H, 6.21; N, 6.02; S, 6.75.

IR (KBr): 3400, 1725, 1650, 740, 695 cm$^{-1}$.

NMR (60 MHz, DMSO-d$_6$): 1.15 (3H, d, J =6.7 Hz, CH$_3$), 7.25 (5H,S, aromatic), 7.38 (5H,S, aromatic).

EXAMPLE 98

[1(S),4S]-1-[N-(Carboxy-3-phenylpropyl)-L-alanyl]-4-[(phenylmethyl) thio]-L-proline (a) cis-4-[(Phenylmethyl) thio]-L-proline, hydrochloride Sodium metal (2.3 g., 0.1 g. atom) is dissolved in 100 ml. of ethanol. To this solution is added, with stirring, 11 ml. (0.094 mole) of benzyl mercaptan, followed by 20 g. (0.046 mole) of trans-N-carbobenzyloxy-4-tosyloxy-L-proline, methyl ester [Patchett et al., "Studies on Hydroxyproline", JACS, Vol. 79, p. 185–192 (1957)]. After stirring at room temperature for 20 hours, the mixture is added to 300 ml. of dichloromethane and 150 ml. of water and stirred until the solids dissolve. The layers are separated and the aqueous phase is extracted with dichloromethane (2×150 ml.; emulsions are partly broken up by adding some methanol and saturated sodium chloride). The combined organic layers are washed with 250 ml. of saturated sodium chloride, dried (MgSO$_4$), and the solvent evaporated. The residue is taken up in 300 ml. of ether and washed with 100 ml. of water. A heavy yellow layer which is insoluble in either phase is separated with the aqueous phase and the ether layer is dried and evaporated to give 17.4 g. of cis-N-carbobenzyloxy-4-[(phenylmethyl)thio]-L-proline, ethyl ester as a pale yellow oil.

The cis-N-carbobenzyloxy-4-[(phenylmethyl)-thio]-L-proline, ethyl ester (16.4 g., 0.042 mole) is saponified in 135 ml. of methanol with 32 ml. (0.064 mole) of 2N sodium hydroxide according to the procedure of Ondetti et al. in Example 44(b) of U.K. Patent Application No. 2,028,327 to give 12.6 g. of a pale yellow oil. The latter (11.7 g.) is dissolved in 60 ml. of acetonitrile and treated with 4.7 g. of 1-adamantanamine to give 12.7 g. of cis-N-carbobenzyloxy-4-[(phenylmethyl)thio]-L-proline, 1-adamantanamine salt as a colorless solid; m.p. 190–192° (s. 182°), $[\alpha]_D^{23} = -20°$ (c=1, methanol).

Anal. calc'd. for C$_{20}$H$_{21}$NO$_4$S.C$_{10}$H$_{17}$N:
C, 68.93; H, 7.33; N, 5.36; S, 6.14.
Found: C, 68.62; H, 7.41; N, 5.47; S, 5.88.

This 1-adamantanamine salt is suspended in 40 ml. of ethyl acetate, stirred, and treated with 30 ml. of 1N hydrochloric acid. The aqueous phase is extracted with additional ethyl acetate (3×40 ml.). The combined organic layers are dried and the solvent evaporated to give 8.9 g. of cis-N-carbobenzyloxy-4-[(phenylmethyl)thio]-L-proline as a viscous, pale yellow oil.

A stirred solution of 7.8 g. (0.021 mole) of cis-N-carbobenzyloxy-4-[(phenylmethyl) thio]-L-proline in 115 ml. of glacial acetic acid is treated with 45 ml. of concentrated hydrochloric acid and heated to reflux for 1 hour. The yellow solution is cooled and the bulk of the acids are removed on a rotary evaporator at 0.2 mm. to give a partly crystalline residue. The latter is triturated with 200 ml. of isopropanol and the evaporation repeated, finally at 0.2 mm. The solid residue is rubbed under ether, cooled overnight, filtered, washed with ether, and dried in vacuo to give 4.9 g. of cis-4-[(phenylmethyl)thio]-L-proline, hydrochloride as a light tan solid; m.p. 130°–132° (s. 125°); $[\alpha]_D^{23} = +7.5°$ (c=1, methanol).

Anal. calc'd. for C$_{12}$H$_{15}$NO$_2$S.HCl:
C, 52.64; H, 5.89; N, 5.12; S, 11.71; Cl, 12.95.
Found C, 51.91; H, 5.78; N, 5.09; S, 11.82; Cl, 12.79.

(b) cis-4-[(Phenylmethyl) thio]-L-proline, methyl ester, hydrochloride

A solution of cis-4-[(phenylmethyl) thio]-L-proline, hydrochloride in methanol is treated with thionyl chloride according to the procedure of Example 95(e) to yield cis-4-[(phenylmethyl) thio]-L-proline, methyl ester, hydrochloride.

(c)
[1(S),4S]-1-[N-(1-Ethoxycarbonyl-3-phenylpropyl)-L-alanyl]-4-[(phenylmethyl)thio]-L-proline, methyl ester N-[1(S)-Ethoxycarbonyl-3-phenylpropyl]-L- alanine and cis-4-[(phenylmethyl) thio]-L- proline, methyl ester, hydrochloride are reacted according to the procedure of Example 95(f) to yield [1(S),4S]-1-[N-(1- ethoxycarbonyl-3-phenylpropyl)-L-alanyl]-4- [(phenylmethyl) thio]-L-proline, methyl ester.

(d) [1(S),4S]-1-[N-(1-Carboxy-3-phenylpropyl)-L-alanyl]-4-[(phenylmethyl)thio]-L-proline A solution of [1(S),4S]-1-[N-(1-ethoxycarbonyl-3-phenylpropyl)-L-alanyl]-4-[(phenylmethyl) thio]-L-proline, methyl ester in ethanol is treated with 1N sodium hydroxide and worked up according to the procedure of Example 95(g) to yield [1(S),4S]-1-[N-(1- carboxy-3-phenylpropyl)-L-alanyl]-4-[(phenylmethyl)thio]-L-proline; $[\alpha]_D^{20} = -51.5°$ (c=1.03, pyridine); R$_f$=0.22, origin (trace), silica gel (ethyl acetate:pyridine:acetic acid:water, 60:20:6:11), visualized with UV and char.

Anal calc'd. for C$_{25}$H$_{30}$N$_2$O$_5$S:
C, 63.81; H, 6.43; N, 5.95; S, 6.81.
Found: C, 63.52; H, 6.43; N, 5.81; S, 6.74.
IR(KBr): 3400, 1720, 1645, 745, 695 cm$^{-1}$.
NMR (60 MHz, DMSO-d$_6$):1.15 (3H,d, J=6.7 Hz, CH$_3$), 3.85 (2H, S, SCH$_2$), 7.25 (5H, S, aromatic), 7.35 (5H,S, aromatic).

EXAMPLE 99

(cis)-1-[N-[(S)-1-Carboxy-3-phenylpropyl]-L-ananyl]-4-phenyl-L-proline (a) cis-4-Phenyl-L-proline, hydrochloride 65 ml. of 3.2 M phenylmagnesium bromide in ether (0.21 mole) is added to a stirred solution of 23.8 g. (0.09 mole) of N-carbobenzyloxy-4-keto-L-proline [Patchett et al., JACS., Vol. 79, p. 189°–192] in 700 ml. of tetrahydrofuran over a period of 15 minutes while the temperature is maintained at 20–25°. A gelatinous precipitate begins to separate after 45 ml. of the Grignard solution is added. After stirring overnight, most of the precipitate dissolves. The mixture is cooled to 15°, treated with a solution of 25 g. of ammonium chloride in 250 ml. of ice water, stirred for one hour, and acidified with 35 ml. of 6N hydrochloric acid. The organic phase is separated and the aqueous layer is extracted twice with 200 ml. of ethyl acetate. The organic phases are combined, dried (MgSO$_4$), filtered, and the solvent evaporated to give 32 g. of tan foam-like solid. This material is treated with 200 ml. of ether—125 ml. of N sodium hydroxide, shaken in a separatory funnel and filtered to remove the gelatinous material at the interface. The aqueous phase is separated, acidified with 22 ml. of 6N hydrochloric acid and extracted with 100 ml. of ethyl acetate. The layers are separated and the aqueous phase is extracted twice 50 ml. ethyl acetate. The organic phases are combined, dried (MgSO$_4$), filtered and the solvent evaporated to give 27.3 g. of a pale yellow foam-like residue. This material is treated with 150 ml. of ether to give a solution from which the product crystallizes. After cooling overnight, the mixture is filtered to give 11.8 g. of colorless solid, m.p. 120°—122°. Crystallization from 22 ml. of ethyl acetate —22 ml. of hexane yields 10.1 g. of N-carbobenzyloxy-cis-4-hydroxy-trans4-phenyl-L-proline; m.p. 121°–123°; $[\alpha]_D^{25} - 32°$ (c, 1% in CHCl$_3$). Additional product can be obtained by concentrating and cooling of the filtrate.

Anal. calc'd. for C$_{19}$H$_{19}$NO$_5$:
C, 66.85; H, 5.61; N, 4.10.
Found: C, 66.67; H, 5.50; N, 3.99.

8.0 g. (0.024 mole) of N-carbobenzyloxy-cis-4-hydroxy-trans-4-phenyl-L-proline is dissolved in 40 ml. of trifluoroacetic acid and the solution is kept overnight at room temperature. The bulk of the trifluoroacetic acid is removed on a rotary evaporator. The yellow-orange liquid residue (16 g.) is taken up in 80 ml. of methylene chloride, and washed with 40 ml. of water. After backextracting the wash with 40 ml. of methylene chloride, the combined organic phaases are dried (MgSO$_4$) and evaporated to give 8.5 g. of N-carbobenzyloxy-3,4-dehydro-4-phenyl-L-proline as a yellow-orange sticky residue.

A solution of 8.5 g. (0.024 mole) of N- carbobenzyloxy-3,4-dehyro-4-phenyl-L-proline in 180 ml. of methanol is treated with a slurry of 3.0 g. of 5% palladium-carbon catalyst in 20 ml. of water and shaken on a Parr hydrogenator for three hours under 3 atmospheres of hydrogen. The hydrogenation appears to be essentially completed within 45 minutes. The catalyst is filtered off under nitrogen, washed with methanol, and the combined filtrates, after treating with 25 ml. of N-hydrochloric acid, are evaporated, finally at 0.2 mm. The pinkish mostly solid residue is taken up in 200 ml. of methanol and the evaporation is repeated. After rubbing under 150 ml. of ether and again repeating the evaporation, the pink solid (5.5 g.) is triturated with 30 ml. of warm acetonitrile (most of the color entered the solvent) and cooled overnight to give 3.9 g. of pale pink solid of cis-4-phenyl-L-proline, hydrochloride; m.p. 115°–117° (foaming) (s. 109°); $[\alpha]_D^{25}$ +5° (c, 1% in methanol); $[\alpha]_D^{25}$ +26° (c, 1% in pyridine).

Anal. calc'd. for C$_{11}$H$_{13}$NO$_2$.HCl.0.75 H$_2$O: C, b 54.77; H, 6.40; N, 5.81; Cl, 14.70
Found: C, 54.45; H, 6.47; N, 5.71; Cl, 14.88.

(b) cis-4-Phenyl-L-proline, methyl ester, hydrochloride

A stirred solution of cis-4-phenyl-L-proline, hydrochloride (1.4 g., 5.91 mmole) in 35 ml. of methanol at −30° under argon is treated with 2.6 ml. (6 eq.) of thionyl chloride added dropwise over 7 minutes and reaction mixture is worked up according to the procedure of Example 95(e). Recrystallization of the crude product from acetonitrile/ether gives 1.02 g. of cis-4-phenyl-L-proline, methyl ester, hydrochloride as a pinkish crystalline solid; m.p. 132°–133° (s, 128°); $[\alpha]_D^{20} = +4.95$ (c=2.12, methanol).

(c) cis-1-[N-[(S)-1-Ethoxycarbonyl-3-phenylpropyl]-L-alanyl]-4-phenyl-L-proline, methyl ester To a cold (0°) solution of N-[1(S)-ethoxycarbonyl-3-phenylpropyl]-L-alanine (747 mg., 2.67 mmole) and cis-4-phenyl-L-proline, methyl ester, hydrochloride (711 mg., 1.1 eq.) in 8 ml. of dimethylformamide under argon is added dropwise a solution of 0.63 ml. (1.1 eq.) of diphenylphosphoryl azide in 1.2 ml. of dimethylformamide. The reaction mixture is worked up according to the procedure of Example 95(f) to yield 940 mg. of cis-1-[N- [(S)-1-ethoxycarbonyl-3-phenylpropyl]-L-alanyl]-4-phenyl-L-proline, methyl ester as a pale yellow oil;$R_f$=0.43 (silica gel, ethyl acetate).

(d)
cis-1-[N-[(S)-1-Carboxy-3-phenylpropyl]-L-alanyl]-4-phenyl-L-proline

A solution of cis-1-[N-[(S)-1-ethoxycarbonyl-3-phenylpropyl]-L- alanyl]-4-phenyl-L- proline, methyl ester (940 mg., 2.01 mmole) in 9 ml. of ethanol under argon is treated with 1N sodium hydroxide (5.03 ml., 2.5 eq.) and worked up according to the procedure of Example 95(g) to yield 701 mg. of cis-1-[N-(S)-1-carboxy-3-phenylpropyl]-L-alanyl]-4-phenyl-L-proline; $[\alpha]_D^{20} = -26.0°$ (c=1.02, pyridine); $R_f$=0.18, origin (trace), 0.62 (trace), silica gel (ethyl acetate:pyridine:acetic acid:water, 60:20:6:1), visualized with UV and char.

Anal. calc'd. for C$_{24}$H$_{28}$N$_2$O$_5$.0.25 H$_2$O: C, 67.19; H, 6.69; N, 6.53. Found: C, 67.17; H, 6.55; N, 6.54.
IR(KBr): 3400, 1725, 1600, 747, 695 cm$^{-1}$.

NMR (60 MHz, DMSO-d$_6$): 1.25 (3H, S, J=1.7 Hz, CH$_3$) 7.27 (5H,S, aromatic), 7.37 (5H,S, aromatic).

EXAMPLE 100

(cis)-1-[N-[(S)-1-Carboxy-3-phenylpropyl]-L-alanyl]-4-cyclohexyl-L-proline (a) cis-4-Cyclohexyl-L-proline hydrochloride A solution of 4.1 g. (0.017 mole) of cis-4-phenyl-L-proline, hydrochloride in 150 ml. of ethanol is treated with 0.6 g. of platinium dioxide and shaken on a Parr hydrogenator for twenty four hours under 3 atmospheres of hydrogen. After filtering off the catalyst under nitrogen and washing with ethanol, the combined filtrates are dried on a rotary evaporator, finally at 0.2 mm. The foamy residue is rubbed under 100 ml. of ether to give a solid and after repeating the evaporation the product is resuspended in 100 ml. of ether, cooled overnight, and filtered to yield 3.5 g. of colorless solid cis-4-cyclohexyl-L-proline, hydrochloride; m.p. 165°–167° (bubbles); (s. 145°); $[\alpha]_D^{25}$ −16° (c, 1% in methanol).

Anal. calc'd. for C$_{11}$H$_{19}$NO$_2$.HCl. 0.25 H$_2$O:
C, 55.45; H, 8.67; N, 5.88; Cl, 14.88
Found: C, 55.70; H, 8.37; N, 5.81; Cl, 14.90.

(b) cis-4-Cyclohexyl-L-proline, methyl ester hydrochloride

A stirred solution of cis-4-cyclohexyl-L-proline, hydrochloride (1.20 g., 5.13 mmole) in 35 ml. of methanol at −30° under argon is treated with 2.3 ml. (6 eq.) of thionyl chloride dropwise over 7 minutes. The reaction mixture is worked up according to the procedure of Example 95(e). Recrystallization from acetonitrile/ether gives 1.07 g. of cis-4-cyclohexyl-L-proline, methyl ester, hydrochloride as a colorless, crystalline material; m.p. 146°–147°; $[\alpha]_D^{20} = -12.7°$ (c=2.09, methanol).

(c)
(cis)-1-[N-[(S)-1-Ethoxycarbonyl-3-phenylpropyl]-L-alanyl]-4-cyclohexyl-L-proline, methyl ester To a cold (0°) solution of N-[1(S)-ethoxycarbonyl -3-phenylpropyl]-L-alanine (700 mg., 2.5 mmole) and cis-4-cyclohexyl-L-proline, methyl ester, hydrochloride (638 mg., 1.1 eq.) in 8 ml. of dry dimethylformamide under argon is added dropwise a solution of diphenylphosphoryl azide (0.60 ml., 1.1 eq.) in 1.2 ml. of dimethylformamide. The reaction mixture is worked up according to the procedure of Example 95(f) to yield 1.04 g. of (cis)-1-[N-[(S)-1-ethoxycarbonyl -3-phenylpropyl]-L- alanyl]-4-cyclohexyl-L-proline, methyl ester as a pale yellow oil; $R_f$=0.42 (silica gel, ethyl acetate).

(d)
(cis)-1-[N-[(S)-1-Carboxy-3-phenylpropyl]-L-alanyl]-4-cyclohexyl-L-proline

A solution of (cis)-1-[N-[(S)-1-ethoxycarbonyl-3 -phenylpropyl]-L-alanyl]-4-cyclohexyl -L-proline, methyl ester (1.04 g., 2.2 mmole) in 10 ml. of ethanol under argon is treated with 1N aqueous sodium hydroxide (5.5 ml., 2.5 eq.) and worked up according to the procedure of Example 95(g) to yield 800 mg. of (cis)-1-[N-[(S)-1-carboxy-3-phenylpropyl]-L-alanyl]-4- cyclohexyl-L-proline; $[\alpha]_D^{20} = -64.7°$ (c=1.08, pyridine); $R_f$ 0.23 origin (trace), 0.70 (trace), silica gel (ethyl acetate:pyridine: acetic acid:water, 60:20:6:11), visualized with UV and Char.

Anal. calc'd. for $C_{24}H_{34}N_2O_5 \cdot 0.2 H_2O$:
C, 66.40; H, 7.97; N, 6.45.
Found: C, 66.57; H, 7.81; N, 6.50.
IR(KBr): 3400, 2920, 2845, 1725, 745, 695 cm$^{-1}$.
NMR (60 MHz-DMSO-d$_6$): 1.17 (3H, d, J=6.7 Hz, CH$_3$), 7.22 (5H,S,aromatic).

EXAMPLE 101

(trans)-1-[N-[(S)-1-Carboxy-3-phenylpropyl]-L-alanyl]-4-(methylthio)-L-proline (a) (trans)-4-(Methylthio)-L-proline, methyl ester, hydrochloride To a stirred solution of (trans)-4- methylthio-L-proline, hydrochloride (1.5 g., 7.59 mmole) [Patchett et al., "Studies on Hydroxyproline", JACS, Vol. 79, p. 185-192 (1957)] in 40 ml. of methanol at −30° under argon is added 3.32 ml. (6 eq.) of thionyl chloride dropwise over 5 minutes. The reaction mixture is worked up according to the procedure of Example 95(e). Recrystallization from acetonitrile/ether gives 630 mg. of (trans)-4- (methylthio-L-proline, methyl ester, hydrochloride as a colorless, crystalline material; m.p. 155-156°; $[\alpha]_D^{20} = -11.3°$ (c=1.71, methanol).

(b) (trans)-1-[N-[(S)-1-Ethoxycarbonyl-3-phenylpropyl]-L-alanyl]-4-(methylthio)-L-proline, methyl ester To a cold (0°) solution of N-[1(S)-ethoxycarbonyl-3-phenylpropyl]-L-alanine (600 mg., 2.15 mmole) and (trans)-4-(methylthio)-L-proline, methyl ester, hydrochloride (500 mg., 1.1 eq.) in 8 ml. of dry dimethylformamide under argon is added dropwise a solution of diphenylphosphoryl azide (0.51 ml., 1.1 eq.) in 1.2 ml. of dimethylformamide. The reaction mixture is worked up according to the procedure of Example 95(f) to yield 700 mg. of (trans)-1-[N-[(S)-1-ethoxycarbonyl-3-phenylpropyl]-L-alanyl]-4-(methylthio)-L-proline, methyl ester as a pale yellow oil; $R_f = 0.35$ (silica gel, ethyl acetate).

(c) (trans)-1-[N-[(S)-1Carboxy-3-phenylpropyl]-L-alanyl]-4-(methylthio)-L-proline A solution of (trans)-1-[N-[(S)-1-ethoxycarbonyl-3-phenylpropyl]-L-alanyl]-4-(methylthio)-L-proline, methyl ester (700 mg., 1.6 mmole) in 9 ml. of ethanol under argon is treated with 1N aqueous sodium hydroxide (4 mmole, 2.5 eq.) and worked up according to the procedure of Example 95(g) to yield 562 mg. of (trans)-1-[N-[(S)-1-carboxy-3-phenylpropyl]-L-alanyl]-4-(methylthio)-L-proline; $[\alpha]_D^{20} = -45.3°$ (c=1.02, pyridine); $R_f$=0.15, origin (trace), 0.50 (trace), silica gel (ethyl acetate:pyridine:acetic acid:water, 60:20:6:11), visualized with UV and (NH$_4$)$_2$SO$_4$/H$_2$SO$_4$ plus heat.

Anal. calc'd. for $C_{19}H_{26}N_2O_5S \cdot 0.5H_2O$:
C, 56.56; H, 6.75; N, 6.94; S, 7.95.
Found: C, 56.32; H, 6.92; N, 7.12; S, 7.94.
IR(KBr): 3420, 1725, 1650, 745, 698 cm$^{-1}$.
NMR (60 MHz, DMSO-d$_6$): 1.18 (3H,d,J=6.7 Hz, CH$_3$), 2.10 (3H,S,SCH$_3$), 7.23 (5H,S,aromatic).

EXAMPLE 102

(cis)-1-[N-[(S)-1-Carboxy-3-phenylpropyl]-L-alanyl]-4-(2-naphthalenyloxy)-L-proline (a) (cis)-4-(2-Naphthalenyloxy)-L-proline Diethylazodicarboxylate (8.82 g., 0.05 mole) dissolved in 10 ml. of tetrahydrofuran is added dropwise over 10 minutes to a stirred solution of 12 g. (0.0338 mole) of N-carbobenzyloxy-trans-4-hydroxy-L-proline, benzyl ester, 7.3 g. (0.05 mole) of 2-hydroxynaphthalene, and 13.3 g. (0.05 mole) of triphenylphosphine in 100 ml. of tetrahydrofuran. After stirring overnight, the solvent is evaporated and the residue taken up in 400 ml. of ethyl ether. Material which crystallizes out overnight at 0° is filtered off, the filtrate is washed with 10% sodium hydroxide (twice), water (twice), dried (Na$_2$SO$_4$), and evaporated. The residue is stirred in 100 ml. of ethyl ether for one hour, filtered, and flash chromatographed on 600 ml. LP-1 silica gel eluted with ethyl ether/pentane. Pure fractions by thin layer chromatography (silica gel, ethyl ether, $R_f$ 0.9) are combined and evaporated to give 12.7 g. of (cis-1-[(phenylmethoxy)carbonyl]-4-(2-naphthalenyloxy)-L-proline, phenylmethyl ester as an oil.

The (cis)-1-[(phenylmethoxy)carbonyl]-4-(2-naphthalenyloxy)-L-proline, phenylmethyl ester (11 g., 22.8 mole) and 1 g. of 10% palladium/ carbon catalyst are hydrogenated in 200 ml. of absolute ethanol in a Parr bottle overnight at 20 psi. The catalyst and precipitated product are filtered off. The filter cake is leached twice with hot methanol. The combined methanol leachates are evaporated to give 1.6 g. of (cis)-4-(2-naphthalenyloxy)-L-proline; m.p. 258°-260° (dec.), $[\alpha]_D^{26} = -14.3°$ [1, water, methanol, sodium hydroxide]. The ethanol filtrate is evaporated to yield an additional 3.0 g. of product.

(b) (cis)-4-(2-Naphthalenyloxy)-L-proline, methyl ester, hydrochloride

To a stirred suspension of (cis)-4-(2-naphthalenyloxy)-L-proline (470 mg., 1.82 mmole) in 20 ml. of methanol at −30° under argon is added 0.8 ml. (6 eq.) of thionyl chloride dropwise over 5 minutes. The reaction mixture is worked up according to the procedure of Example 95(e). Recrystallization from acetonitrile/ether gives 479 mg. of (cis)-4-(2-naphthalenyloxy)-L-proline, methyl ester, hydrochloride as a light tan solid; m.p. 180°-181°; $[\alpha]_D^{20} = +24.1°$ (c=1.55, methanol).

(c) (cis)-1-[N-[(S)-1-Ethoxycarbonyl-3-phenylpropyl]-L-alanyl]-4-(2-naphthalenyloxy)-L-proline, methyl ester To a cold (0°) solution of N-[1(S)-ethoxycarbonyl-3-phenylpropyl]-L-alanine (372 mg., 1.32 mmole) and (cis)-4-(2-naphthalenyl- oxy)-L-proline, methyl ester, hydrochloride (450 mg., 1.1 e1) in 7.5 ml. of dry dimethylformamide under argon is added dropwise a solution of diphenylphosphoryl azide (0.32 ml., 1.1 eq.) in 1.2 ml. of dimethylformamide. The reaction mixture is worked up according to the procedure of Example 95(f) to yield 480 mg. of (cis)-1-[N-[(S)-1-ethoxycarbonyl-3-phenylpropyl]-L-alanyl]-4-(2-naphthalenyloxy)-L-proline, methyl ester as a pale yellow foam; $R_f$=0.25 (silica gel, ethyl acetate).

(d)
(cis)-1-[N-[(S)-1-Carboxy-3-phenylpropyl]-L-alanyl]-4-(2-naphthalenyloxy)-L-proline A solution of (cis)-1-[N-[(S)-1-ethoxycarbonyl-3-phenylpropyl]-L-alanyl]-4-(2-naphthalenyloxy)-L-proline, methyl ester (480 mg., 0.90 mmole) in 8 ml. of ethanol under argon is treated with 1 N aqueous sodium hydroxide (2.3 mmole, 2.5 eq.) and worked up according to the procedure of Example 95(g) to yield 376 mg. of (cis)-1-[N-[(S)-1-carboxy-3-phenylpropyl]-L-alanyl]-4-(2-naphthalenyloxy)-L-proline; $[\alpha]_D^{20} = -5.9$ (c=1.03, pyridine); $R_f=0.24$, origin (trace), silica gel (ethyl acetate:pyridine:acetic acid:water, 10:20:6:11), visualized with UV and $(NH_4)_2 SO_4/H_2SO_4$ plus heat.

Anal. calc'd. for $C_{28}H_{30}N_2O_6 \cdot 0.4\ H_2O$:
C, 67.56; H, 6.24; N, 5.62.
Found: C, 67.59; H, 6.11; N, 5.85.
IR(KBr): 3400, 1725, 1655, 1630, 1600, 745, 695 cm$^{-1}$.
NMR (100 MHz, DMSO-d$_6$): 1.27 (3H,d,J=6.7 Hz, CH$_3$),
7.0–7.96 (12H, M, aromatic).

EXAMPLE 103
(cis)-1-[N-[(S)-1-Carboxy-3-phenylpropyl]-L-alanyl]-4-[(phenylmethhyl)amino]-L-proline

(a) (cis)-4-[(t-Butoxycarbonyl)(phenylmethyl)-amino]-L-proline, ethyl ester Ethyl iodide (15.0 g., 0.1 mole) is added dropwise to a stirred suspension of sodium bicarbonate (8.4 g., 0.1 mole) and N-carbobenzyloxy-4-keto-L-proline (5.2 g., 0.02 mole) in 100 ml. of diemthylformamide at 5°. After the addition is completed, the reaction mixture is stirred at room temperature for 60 hours. It is then concentrated in vacuo and 200 ml. of water is added to the residue. The product is extracted with ether (3×200 ml.), washed with saturated sodium chloride, dried (MgSO$_4$), filtered, and concentrated in vacuo to yield 4.7 g. of N-carbobenzyloxy-4-keto-L-proline, ethyl ester; $R_f=0.58$ (silica gel, ethyl acetate).

The N-carbobenzyloxy-4-keto-L-proline, ethyl ester (5.7 g., 0.02 mole) and benzylamine (3.2 g., 0.03 mole) are dissolved in 200 ml. of benzene. To this is added 8 g. of crushed 4A° molecular sieves. The mixture is stirred for 3 hours at room temperature, the molecular sieves are filtered off, and the filtrate is concentrated in vacuo. The crude imine is dissolved in 200 ml. of ethyl acetate and reduced in a Parr apparatus at 40 psi using platinum dioxide catalyst. After 4 hours, the reaction mixture is removed from the Parr apparatus and filtered through celite. The filtrate is concentrated in vacuo to yield 5.7 g. of crude (cis)-N-carbobenzyloxy-4-[(phenylmethyl)amino]-L-proline, ethyl ester, The (cis)-N-carbobenzyloxy-4-[(phenylmethyl)amino]-L-proline, ethyl ester (2.14 g.) is dissolved in 100 ml. of tetrahydrofuran and cooled to 5°. Ditertiarybutyl dicarbonate (1.22 g.) is added portionwise and the reaction mixture is stirred at room temperature overnight. It is then concentrated in vacuo, dissolved in ethyl acetate and washed with aqueous sodium bicarbonate, water and saturated brine. The ethyl acetate solution is dried (MgSO$_4$), filtered and concentrated in vacuo to yield 2.89 g. of (cis)-N-carbobenzyloxy-4-[(t-butoxycarbonyl)(phenylmethyl)amino]-L-proline, ethyl ester.

The (cis)-N-carbobenzyloxy-4-[(t-butoxycarbonyl)(phenylmethyl)amino]-L-proline, ethyl ester (2.89 g.) is dissolved in 100 ml. of absolute ethanol and reduced on the Parr apparatus for 1 hour using a scoop of 10% palladium/carbon catalyst. The reaction is vented two times at 20 minute intervals and then repressurized to 30 psi. The reaction mixture is filtered through celite and concentrated in vacuo to yield 2.0 g. of crude product. This material is purified by absorbing on 5 g. of silica (60–200 mesh), placing on a 50 g. pad of silica and filtering through with 500 ml. of hexane, 500 ml. (1:1) hexane:ether, and 500 ml. of ether. The product is eluted with ether to give 1.4 g. of (cis)-4-[(t-butoxycarbonyl)(phenylmethyl)amino]-L-proline, ethyl ester; $R_f=0.25$ (silica gel, ethyl acetate).

(b)
(cis)-1-[N-[(S)-1-Ethoxycarbonyl-3-phenylpropyl]-L-alanyl]-4-[(t-butoxycarbonyl)(phenylmethyl)amino]-L-proline, ethyl ester To a cold (0°) solution of N-[1(S)-ethoxycarbonyl-3-phenylpropyl]-L-alanine (728 mg., 2.6 mmole) and (cis)-4-[(t-butoxycarbonyl)(phenylmethyl)amino]-L-proline, ethyl ester (1.0 g., 1.1 eq.) in 9 ml. of dry dimethylformamide under argon is added dropwise a solution of diphenylphosphoryl azide (0.62 ml., 1.1 eq.) in 1.2 ml. of dimethylformamide. The reaction mixture is worked up according to the procedure of Example 95(f) to yield 1.27 g. of (cis)-1-[N-[(S)-1-ethoxycarbonyl-3-phenylpropyl]-L-alanyl]-4-[(t-butoxycarbonyl)(phenylmethyl)amino]-L-proline, ethyl ester as a pale yellow oil; $R_f=0.47$ (silica gel, ethyl acetate).

(c)
(cis)-1-[N-[(S)-1-Ethoxycarbonyl-3-phenylpropyl]-L-alanyl]-4-[(phenylmethyl)amino]-L-proline, ethyl ester A solution of (cis)-1-[N-[(S)-1-ethoxycarbonyl-3-phenylpropyl]-L-alanyl]-4-[(t-butoxycarbonyl)(phenylmethyl)amino]-L-proline, ethyl ester (1.27 g., 2.08 mmole) in 40 ml. of redistilled trifluoroacetic acid is stirred at 0° for 30 minutes. The bulk of the trifluoroacetic acid is removed at reduced pressure on a rotary evaporator and the residue is dissolved in ethyl acetate. The resulting solution is washed with 1 N sodium bicarbonate (twice) and brine. After drying over anhydrous MgSO$_4$, the solvent is removed at reduced pressure to give 1.07 g. of (cis)-1-[N-[(S)-1-ethoxycarbonyl-3-phenylpropyl]-L-alanyl]-4-[(phenylmethyl)amino]-L-proline, ethyl ester; $R_f=0.18$ (silica gel, ethyl acetate).

(d)
(cis)-1-[N-[(S)-1-Carboxy-3-phenylpropyl]-L-alanyl]-4-[(phenylmethyl)amino]-L-proline A solution of (cis)-1-[N-[(S)-1-ethoxycarbonyl-3-phenylpropyl]-L-alanyl]-4-[(phenylmethyl)amino]-L-proline, ethyl ester (1.07 g., approx. 2.08 mmole) in 9 ml. of ethanol under argon is treated with 1 N aqueous sodium hydroxide (5.3 mmole, 2.5 eq.) and worked up according to the procedure of Example 95(g) to yield 811 mg. of (cis)-1-[N-[(S)-1-carboxy-3-phenylpropyl]-L-alanyl]-4-[(phenylmethyl)amino]-L-proline; $[\alpha]_D^{20} = -37.4°$ (c=1.23, pyridine); $R_f=0.30$ silica gel (n-butanol:acetic acid:water, 4:1:1), visualized with UV and $(NH_4)_2SO_4/H_2SO_4$ plus heat.

Anal. calc'd. for $C_{25}H_{31}N_3O_5 \cdot 0.9\ H_2O$:
C, 63.92; H, 7.04; N, 8.94.
Found: C, 63.98; H, 6.89; N, 8.93.
IR (KBr): 3400, 1710, 1640, 740, 693 cm$^{-1}$.
NMR (100 MHz), CD$_3$CO$_2$D): 1.63 (3H,d,J=6.7 Hz, CH$_3$), 7.24(5H,S,aromatic), 7.46(5H,S,aromatic).

EXAMPLE 104

(S,S,S)-7-[2-[(1-Carboxy-3-phenylpropyl)amino]-1-oxopropyl]-1,4-dithia-7-azaspiro[4.4]nonane-8-carboxylic acid (a) (S)-1,4-Dithia-7-azaspiro[4.4]nonane-8-carboxylic acid, methyl ester, hydrochloride To a stirred solution of (S)-1,4-dithia-7-azaspiro[4.4]nonane-8-carboxylic acid, hydrochloride (3.05 g., 12.6 mmole) [prepared as set forth by Krapcho in Example 9 parts (a) to (c) of U.K. Patent Application No. 2,039,478 except that hydrochloric acid is employed in place of hydrogen bromide in part (c)] in 60 ml. of methanol at $-30°$ under argon is added dropwise 5.5 ml. (6 eq.) of thionyl chloride over 10 minutes. The reaction mixture is worked up according to the procedure of Example 95(e). Recrystallization from methanol/ether gives 1.83 g. of (S)-1,4-dithia-7-azaspiro[4.4]nonane-8-carboxylic acid, methyl ester, hydrochloride as a light tan solid; m.p. 137°–138° (s. 134°); $[\alpha]_D^{20} = +12.67°$ (c=1.63, methanol).

(b) (S,S,S)-7-[2-[(1-Ethoxycarbonyl-3-phenylpropyl)amino]-1-oxopropyl]-1,4-dithia-7-azaspiro[4.4]-nonane-8-carboxylic acid, methyl ester To a cold (0°) solution of N-[1(S)-ethoxycarbonyl-3-phenylpropyl]-L-alanine (720 mg., 2.57 mmole) and (S)-1,4-dithia-7-azaspiro[4.4]nonane-8-carboxylic acid, methyl ester, hyrochloride (725 mg., 1.1 eq.) in 8 ml. of dimethylformamide under argon is added dropwise a solution of diphenylphosphoryl azide in 1 ml. of dimethylformamide. The reaction mixture is worked up according to the procedure of Example 95(f) to yield 660 mg. of (S,S,S)-7-[2-[(1-ethoxycarbonyl-3-phenylpropyl)amino]-1-oxopropyl]-1,4-dithia-7-azaspiro[4.4]nonane-8-carboxylic acid, methyl ester as a yellow oil; $R_f = 0.37$ (silica gel, ethyl acetate).

(c) (S,S,S)-7-[2-[(1-Carboxy-3-phenylpropyl)amino]-1-oxopropyl]-1,4-dithia-7-azaspiro[4.4]nonane-8-carboxylic acid A solution of (S,S,S)-7-[2-[(1-ethoxycarbonyl-3-phenylpropyl)amino]-1-oxopropyl]-1,4-dithia-7-azaspiro[4.4]nonane-8-carboxylic acid, methyl ester (660 mg., 1.37 mmole) in 8 ml. of ethanol under argon is treated with 1 N sodium hyroxide (3.4 ml., 2.5 eq.) and worked up according to the procedure of Example 95(g) to yield 583 mg. of (S,S,S)-7-[2-[(1-carboxy-3-phenylpropyl)amino]-1-oxopropyl]-1,4-dithia-7-azaspiro[4.4]nonane-8-carboxylic acid; $[\alpha]_D^{20} = +1.96$ (c=1.5, methanol); $R_f = 0.14$, origin (trace), silica gel (ethyl acetate:pyridine:acetic acid:water, 60:20:6:11), visualized with UV and char.

Anal. calc'd. for $C_{20}H_{26}N_2O_5S_2$:
C, 54.77; H, 5.98; N, 6.39; S, 14.62.
Found: C, 54.92; H, 5.93; N, 6.52; S, 14.44.
IR(KBr): 3410, 1725, 1650, 745, 697, 693 cm$^{-1}$.
NMR (60 MHz, DMSO-d$_6$): 1.15 (3H,d, J=6.7 Hz, CH$_3$) 3.30 (4H,S,SCH$_2$CH$_2$S), 7.15 (5H,S,aromatic).

EXAMPLE 105

(S,S,S)-7-[2-[(1-Ethoxycarboxy-3-phenylpropyl)amino]-1-oxopropyl]-1,4-dithia-7-azaspiro[4.4]-nonane-8-carboxylic acid (a) (S)-1,4-Dithia-7-azaspiro[4.4]nonane-8-carboxylic acid, diphenylmethyl ester, p-toluenesulfonate An aqueous solution of 5 g. of (S)-1,4-dithia-7-azaspiro[4.4]nonane-8-carboxylic acid, hydrochloride is passed through an AG11A8 column (bed volume: 160 ml.) by eluting with water. The product containing fractions are combined and treated with 3.93 g. of p-toluenesulfonic acid monohydrate and evaporated to dryness. Toluene is then added and the mixture is evaporated to dryness. Trituration with ether gives (S)-1,4-dithia-7-azaspiro[4.4]nonane-8-carboxylic acid, p-toluenesulfonate.

To a solution of (S)-1,4-dithia-7-azaspiro[4.4]nonane-8-carboxylic acid, p-toluenesulfonate (6.0 g.) in 30 ml. of anhydrous dimethylformamide at 50 ° under argon is added a dimethylformamide solution of diphenyldiazomethane (3.6) portionwise. After 10 minutes at 50°, the solvent is removed under reduced pressure. The residue is dissolved in ethyl acetate and precipitated with ether. The solvent is then decanted and the residue triturated with ethyl acetate/ether to give (S)-1,4-dithia-7-azaspiro [4.4]nonane-8-carboxylic acid, diphenylmethyl ester, p-toluenesulfonate.

(b) (S,S,S)-7-[2-[(1-Ethoxycarbonyl-3-phenylpropyl)amino]-1-oxopropyl]-1,4-dithia-7-azaspiro[4.4]nonane-8-carboxylic acid, diphenylmethyl ester To a cold (0°) solution of N-[1(S)-ethoxycarbonyl-3-phenylpropyl]-L-alanine (720 mg., 2.57 mmole) and (S)-1,4-dithia-7-azaspiro[4.4]nonane-8-carboxylic acid, diphenylmethyl ester, p-toluenesulfonate (1.06 g., 1.1 eq.) in 8 ml. of dry dimethylformamide under argon is added dropwise a solution of 0.61 ml. (1.1 eq.) of diphenylphosphoryl azide in 1 ml. of dimethylformamide. The reaction mixture is worked up according to the procedure of Example 95(f) to yield (S,S,S)-7-[2-[(1-ethoxycarbonyl-3-phenylpropyl)amino]-1-oxopropyl]-1,4-dithia-7-azaspiro[4.4]nonane-8-carboxylic acid, diphenylmethyl ester.

(c) (S,S,S)-7-[2-[(1-Ethoxycarbonyl-3-phenylpropyl)amino]-1-oxopropyl]-1,4-dithia-7-azaspiro-[4,4]nonane-8-carboxylic acid A solution of (S,S,S)-7-[2-[(1-ethoxycarbonyl-3-phenylpropyl)amino]-1-oxopropyl]-1,4-dithia-7-azaspiro[4.4]nonane-8-carboxylic acid, diphenylmethyl ester (800 mg.) in a mixture of trifluoroacetic acid (15 ml.) and anisole (3 ml.) is stirred at 0° for 30 minutes. The solvent is removed at reduced pressure and the residue applied to an AG 50W-X2(H$^+$) column. After washing with water, the column is eluted with aqueous pyridine. The fractions containing the product are combined and lyophilized to yield (S,S,S)-7-[2-[(1-ethoxycarbonyl-3-phenylpropyl)amino]-1-oxopropyl]-1,4-dithia-7-azaspiro[4.4]nonane-8-carboxylic acid.

EXAMPLES 106–118

Following the procedure of Examples 95 to 104, but employing the substituted proline ester shown in Col. I one obtains the diester shown in Col. II which is then treated with sodium hydroxide according to the procedure of Example 95(g) to yield the corresponding diacid.

Col. I
H—R₄·HCl

Col. II

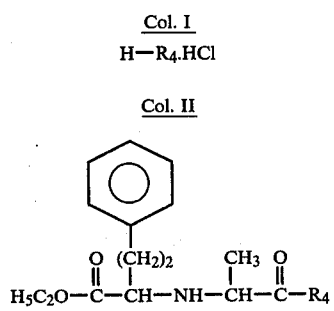

| Example | R₄ |
|---|---|
| 106 | 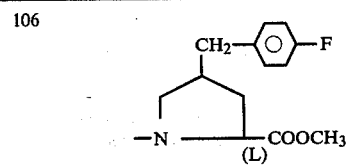 |
| 107 | 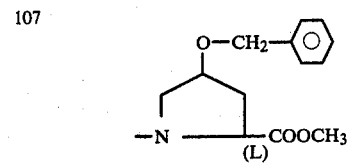 |
| 108 | 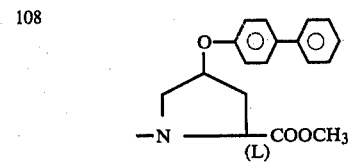 |
| 109 | 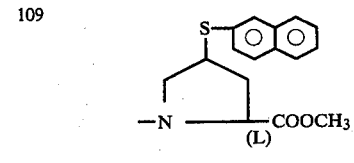 |
| 110 | 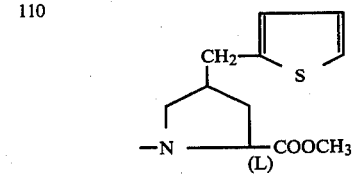 |
| 111 | 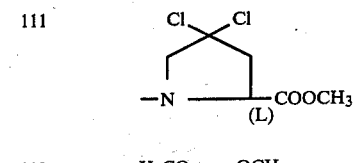 |
| 112 | 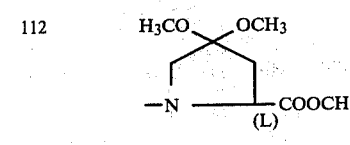 |

-continued

| Example | R₄ |
|---|---|
| 113 | ![structure with O O spiro ring] -N————COOCH₃ (L) |
| 114 | H₃CS SCH₃ -N————COOCH₃ (L) |
| 115 | S S spiro -N————COOCH₃ (L) |
| 116 | O—⌬ -N————COOCH₃ (L) |
| 117 | S—CH₂—⌬—F -N————COOCH₃ (L) |
| 118 | ⌬ CH-CH₂CH₂ -N————COOCH₃ (L) |

In a similar manner, by employing the corresponding benzyl ester of the substituted prolines of examples 95 to 103 and 106 to 119 within the procedure of Example 105, the corresponding monoester product is obtained.

EXAMPLE 119

1000 tablets each containing the following ingredients:

| | |
|---|---|
| (S,S,S)-7-[2-[(1-Ethoxycarbonyl-3-phenylpropyl)-amino]-1-oxopropyl]-1,4-dithia-7-azaspiro[4.4]-nonane-8-carboxylic acid | 100 mg. |
| Corn Starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the (S,S,S)-7-[2-[(1-ethoxycarbonyl-3-phenylpropyl)amino]-1-oxopropyl]-1,4-dithia-7-azaspiro[4.4]nonane-8-carboxylic acid and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner tablets containing 100 mg. of the product of any of Examples 2 to 104 and 106 to 118 can be prepared.

EXAMPLE 120

1000 tablets each containing the following ingredients:

| | |
|---|---|
| 1-[N—(1-(S)-Carboxy-3-phenylpropyl)-L-alanyl]-4-(S)-(phenylthio)-L-proline | 50 mg. |
| Lactose | 25 mg. |
| Avicel | 38 mg. |
| Cornstarch | 15 mg. |
| Magnesium stearate | 2 mg. |
| | 130 mg. | are prepared by admixing the 1-[N-(1-(S)-carboxy-3-phenylpropyl)-L-alanyl]-4-(S)-(phenylthio)-L-proline, lactose and Avicel and then blending with the corn starch. Magnesium stearate is added. The dry mixture is compressed in a tablet press to form 1000 130 mg. tablets each containing 50 mg. of active ingredient. The tablets are coated with a solution of Methocel E 15 (methyl cellulose) including as a color a lake containing yellow #6.

In a similar manner tablets containing 50 mg. of the product of any of Examples 1 to 94 and 96 to 118 can be prepared.

EXAMPLE 121

Two piece #1 gelatin capsules each containing 100 mg. of 1-[N-(1-(S)-carboxy-3-phenylpropyl)-L-alanyl]-4-(S)-(phenylthio)-L-proline are filled with a mixture of the following ingredients:

| | |
|---|---|
| 1-[N—(1-(S)-Carboxy-3-phenylpropyl)-L-alanyl]-4-(S)-(phenylthio)-L-proline | 100 mg. |
| Magnesium stearate | 7 mg. |
| Lactose | 193 mg. |

In a similar manner capsules containing 100 mg. of the product of any of Examples 1 to 94 and 96 to 118 can be prepared.

EXAMPLE 122

An injectable solution is prepared as follows:

| | |
|---|---|
| (cis)-1-[N—[1-(S)-Carboxy-3-phenylpropyl]-L-alanyl-4-phenyl-L-proline | 500 g. |
| Methyl paraben | 5 g. |
| Propyl paraben | 1 g. |
| Sodium chloride | 25 g. |
| Water for injection qs. | 5 l |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

In a similar manner an injectable solution containing 100 mg. of active ingredients per ml. of solution can be prepared for the product of any of Examples 1 to 98 and 100 to 118.

EXAMPLE 123

1000 tablets each containing the following ingredients:

| | |
|---|---|
| (S,S,S)-7-[2-[(1-Ethoxy-carbonyl-3-phenylpropyl)amino]-1-oxopropyl]-1,4-dithia-7-aza-spiro[4.4]nonane-8-carboxylic acid | 100 mg. |
| Avicel (microcrystalline cellulose) | 100 mg. |
| Hydrochlorothiazide | 12.5 mg. |
| Lactose U.S.P. | 113 mg. |
| Corn starch U.S.P. | 17.5 mg. |
| Stearic acid U.S.P. | 7 mg. |
| | 350 mg. | are prepared from sufficient bulk quantities by slugging the (S,S,S)-7-[2-[(1-ethoxycarbonyl-3-phenylpropyl)amino]-1-oxopropyl]-1,4-dithia-7-azaspiro[4.4]nonane-8-carboxylic acid, Avicel and a portion of the stearic acid. The slugs are ground and passed through a #2 screen, then mixed with the hydrochlorothiazide, lactose, corn starch and remainder of the stearic acid. The mixture is compressed into 350 mg. capsule shaped tablets in a tablet press. The tablets are scored for dividing in half.

In a similar manner tablets can be prepared containing 100 mg. of the product of any of Examples 2 to 104 and 106 to 118.

What is claimed is:

1. A compound of the formula

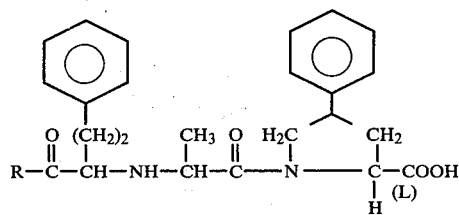

and a pharmaceutically acceptable salt thereof wherein R is hydroxy or ethoxy.

2. A compound of the formula

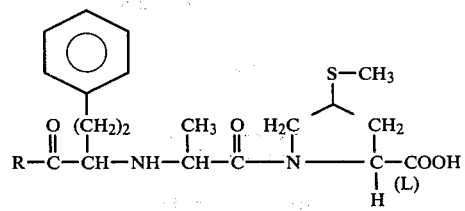

and a pharmaceutically acceptable salt thereof wherein R is hydroxy or ethoxy.

3. A compound of the formula

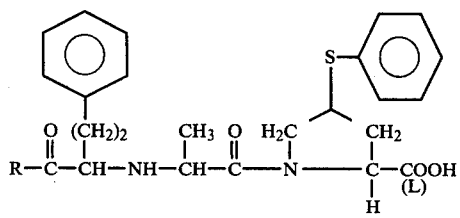
and a pharmaceutically acceptable salt thereof wherein R is hydroxy or ethoxy.
4. The compound of claim 1, (cis)-1-[N-[(S)-1-carboxy-3-phenylpropyl]-L-alanyl]-4-phenyl-L-proline.
5. The compound of claim 2, (trans)-1-[N-[(S)-1-carboxy-3-phenylpropyl]-L-alanyl]-4-(methylthio)-L-proline.
6. The compound of claim 3, [1(S),4R]-1-[N-(1-carboxy-3-phenylpropyl)-L-alanyl]-4-(phenylthio)-L-proline.
* * * * *

UNITED STATES PATENT AND TRADEMARK OFFICE
CERTIFICATE OF CORRECTION

PATENT NO. : 4,462,943
DATED : July 31, 1984
INVENTOR(S) : Edward W. Petrillo, Jr. et al.

It is certified that error appears in the above-identified patent and that said Letters Patent are hereby corrected as shown below:

Column 4, line 14, delete "fluor" and insert --fluoro --.
Column 5, line 47, delete " and q is". Column 5, line 50, after the formula should be added -- and q is --. Column 5, line 59, delete the numeral "13". Column 5, line 59, after $-(CH_2)_q$ (first occurrence) insert a dash. Column 9, line 27, delete "thionly" and insert --thionyl--. Column 13, line 52, delete "of" and insert -- or --. Column 15, line 5, delete "riamterene" and insert -- triamterene --. Column 15, line 27, delete "1-[N-(bl(S)-" and insert -- 1-[N-(1-(S)- --.
Column 19, line 45, delete "watermethanol" and insert -- water-methanol --. Column 20, line 55, delete "ehtyl" and insert -- ethyl --. Column 39, line 20, delete "1-[N-Carboxy" and insert -- 1-[N-(1-Carboxy --. Column 45, line 17, "g.atom" should read --g. atom--. Column 52, line 60, delete "1.1 el" and insert -- 1.1 eg. --.

Signed and Sealed this

Fifth Day of November 1985

[SEAL]

Attest:

DONALD J. QUIGG

Attesting Officer

Commissioner of Patents and Trademarks